United States Patent
Gupta et al.

(10) Patent No.: US 10,285,675 B2
(45) Date of Patent: May 14, 2019

(54) TISSUE ISOLATOR

(71) Applicant: Veol Medical Technologies Pvt. Ltd., Navi Mumbai (IN)

(72) Inventors: Arvind Kumar Gupta, Ballia (IN); Mangesh Patankar, Navi Mumbai (IN); Nikhil Ramchandra Katre, Thane (IN); Debasish Pradhan, Sambalpur (IN); Dinesh Diwakar, Mumbai (IN)

(73) Assignee: Veol Medical Technologies Pvt. Ltd., Navi Mumbai (IN)

( * ) Notice: Subject to any disclaimer, the term of this patent is extended or adjusted under 35 U.S.C. 154(b) by 186 days.

(21) Appl. No.: 15/237,409

(22) PCT Filed: Mar. 27, 2015

(86) PCT No.: PCT/IN2015/000151
§ 371 (c)(1),
(2) Date: Aug. 15, 2016

(87) PCT Pub. No.: WO2015/151117
PCT Pub. Date: Oct. 8, 2015

(65) Prior Publication Data
US 2017/0252026 A1    Sep. 7, 2017

(30) Foreign Application Priority Data

Apr. 3, 2014  (IN) .......... 1262/MUM/2014
May 26, 2014  (IN) .......... 1749/MUM/2014
(Continued)

(51) Int. Cl.
*A61B 17/00* (2006.01)
*A61B 17/34* (2006.01)
*A61B 90/40* (2016.01)

(52) U.S. Cl.
CPC .... *A61B 17/00234* (2013.01); *A61B 17/3423* (2013.01); *A61B 17/3462* (2013.01);
(Continued)

(58) Field of Classification Search
CPC ...... A61B 17/3423; A61B 2017/00287; A61B 2017/320024; A61B 2090/3937
See application file for complete search history.

(56) References Cited

U.S. PATENT DOCUMENTS 4,950,222 A * 8/1990 Scott .................... A61G 10/005
                                                    312/1
5,524,633 A * 6/1996 Heaven ............ A61B 17/00234
                                                    128/DIG. 24
(Continued)

FOREIGN PATENT DOCUMENTS

DE         4405831 A1    8/1995
JP        H08140983 A    6/1996
WO     WO-2011-110836    9/2011

OTHER PUBLICATIONS

Machine Translation of DE-4405831-A1 (publication date of Aug. 24, 1995 per the IDS of Aug. 31, 2018) provided by EPO and obtained by the examiner on Jan. 15, 2019. (Year: 1995).*
(Continued)

*Primary Examiner* — Ryan J. Severson
(74) *Attorney, Agent, or Firm* — Blank Rome LLP

(57) ABSTRACT

A biocompatible tissue isolator is used to isolate and extract tissue during a surgical procedure. A method of using the tissue isolator for isolating and extracting morcellated tissue during the surgery.

21 Claims, 32 Drawing Sheets

(30) Foreign Application Priority Data

| May 26, 2014 | (IN) | 1750/MUM/2014 |
| Jul. 9, 2014 | (IN) | 2241/MUM/2014 |
| Aug. 22, 2014 | (IN) | 2697/MUM/2014 |
| Sep. 15, 2014 | (IN) | 2933/MUM/2014 |
| Nov. 5, 2014 | (IN) | 3482/MUM/2014 |

(52) U.S. Cl.
CPC ........... *A61B 17/3474* (2013.01); *A61B 90/40* (2016.02); *A61B 2017/00287* (2013.01); *A61B 2017/3466* (2013.01)

(56) References Cited

U.S. PATENT DOCUMENTS

| 5,728,041 | A * | 3/1998 | Fowler, Jr. | A61G 10/02 600/21 |
| 6,270,505 | B1 | 8/2001 | Yoshida et al. | |
| 6,752,822 | B2 | 6/2004 | Jespersen | |
| 8,579,914 | B2 * | 11/2013 | Menn | A61B 17/00234 606/114 |
| 8,585,712 | B2 * | 11/2013 | O'Prey | A61B 17/26 606/114 |
| 8,652,147 | B2 * | 2/2014 | Hart | A61B 17/00234 606/114 |
| 8,721,658 | B2 * | 5/2014 | Kahle | A61B 17/00234 606/114 |
| 8,821,377 | B2 * | 9/2014 | Collins | A61B 17/221 128/898 |
| 8,920,431 | B2 * | 12/2014 | Shibley | A61B 17/00234 606/114 |
| 8,956,286 | B2 * | 2/2015 | Shibley | A61M 13/003 600/235 |
| 9,044,210 | B1 * | 6/2015 | Hoyte | A61B 17/00234 |
| 9,370,378 | B2 * | 6/2016 | O'Prey | A61B 17/26 |
| 9,468,452 | B2 * | 10/2016 | Menn | A61B 17/00234 |
| 9,579,115 | B2 * | 2/2017 | Kahle | A61B 17/00234 |
| 9,655,644 | B2 * | 5/2017 | Collins | A61B 17/00234 |
| 9,872,674 | B2 * | 1/2018 | Lehmann | A61B 17/221 |
| 9,877,739 | B2 * | 1/2018 | Hoyte | A61B 17/00234 |
| 9,877,740 | B2 * | 1/2018 | Sullivan | A61B 17/32002 |
| 9,901,329 | B1 * | 2/2018 | Polo | A61B 17/32002 |
| 9,974,528 | B2 * | 5/2018 | Taylor | A61B 17/00234 |
| 9,974,554 | B2 * | 5/2018 | Antonelli | A61B 17/221 |
| 9,986,986 | B2 * | 6/2018 | Radl | A61B 17/00234 |
| 2003/0139767 | A1 * | 7/2003 | Jespersen | A61B 17/00234 606/205 |
| 2004/0097960 | A1 * | 5/2004 | Terachi | A61B 50/31 606/114 |
| 2006/0241651 | A1 * | 10/2006 | Wilk | A61B 17/3423 606/108 |
| 2007/0088370 | A1 * | 4/2007 | Kahle | A61B 17/00234 606/114 |
| 2007/0135781 | A1 * | 6/2007 | Hart | A61B 17/00234 604/327 |
| 2011/0011410 | A1 * | 1/2011 | Desai | A61B 17/0293 128/898 |
| 2011/0190780 | A1 * | 8/2011 | O'Prey | A61B 17/26 606/114 |
| 2012/0158010 | A1 * | 6/2012 | Menn | A61B 17/00234 606/114 |
| 2013/0184536 | A1 | 7/2013 | Shibley et al. | |
| 2013/0253267 | A1 * | 9/2013 | Collins | A61B 17/221 600/104 |
| 2014/0046337 | A1 * | 2/2014 | O'Prey | A61B 17/26 606/114 |
| 2014/0058403 | A1 * | 2/2014 | Menn | A61B 17/00234 606/114 |
| 2014/0135788 | A1 * | 5/2014 | Collins | A61B 17/00234 606/114 |
| 2014/0236167 | A1 * | 8/2014 | Shibley | A61B 17/00234 606/114 |
| 2014/0236168 | A1 * | 8/2014 | Shibley | A61B 17/0218 606/114 |
| 2014/0249541 | A1 * | 9/2014 | Kahle | A61B 17/00234 606/114 |
| 2015/0297254 | A1 * | 10/2015 | Sullivan | A61B 17/32002 606/114 |
| 2015/0305728 | A1 * | 10/2015 | Taylor | A61B 17/00234 606/114 |
| 2015/0305764 | A1 * | 10/2015 | Hoyte | A61B 17/00234 606/114 |
| 2015/0320409 | A1 * | 11/2015 | Lehmann | A61B 17/221 600/109 |
| 2016/0066934 | A1 * | 3/2016 | Antonelli | A61B 17/221 606/128 |
| 2016/0242751 | A1 * | 8/2016 | Bonadio | A61B 17/00234 |
| 2017/0252026 | A1 * | 9/2017 | Gupta | A61B 17/00234 |

OTHER PUBLICATIONS

International Search Report issued in PCT/IN2015/000151 dated Feb. 1, 2016.

Supplemental European Search Report issued in EP15772614 dated Oct. 19, 2017.

* cited by examiner

TISSUE ISOLATOR

This application claims the priority of International Patent Application No. PCT/IN2015/000151, filed Mar. 27, 2015, which claims priority to Indian Patent Application No. 1262/MUM/2014, FILED Apr. 3, 2014, Indian Patent Application No. 1749/MUM/2014, FILED May 26, 2014, Indian Patent Application No. 1750/MUM/2014, filed May 26, 2014, Indian Patent Application No. 2241/MUM/2014, filed Jul. 9, 2014, Indian Patent Application No. 2697/MUM/2014, Aug. 22, 2014, Indian Patent Application No. 2933/MUM/2014, filed Sep. 15, 2014, and Indian Patent Application No. 3482/MUM/2014, filed Nov. 5, 2014, each of which is incorporated in their entirety.

FIELD OF THE INVENTION

The present invention relates, in general, to the field of biomedical devices used in surgical procedure and, in particular, to a tissue isolator designed to isolate tissue for morcellation and prevent seeding of benign or potentially cancerous tissue during the morcellation procedure. The present invention further prevents accidental damage to the surrounding healthy tissue.

BACKGROUND OF THE INVENTION

In the prior art, various types of pouches or bags have been developed to allow for the removal of tissue through a small opening, orifice, or port in an surgical procedure such as laparoscopic procedure. Tissue bags have also been considered for the morcellation of tissue inside the bag for its safe removal. Unfortunately, many surgical techniques using bags for morcellation are difficult to accomplish due to various constraints present in the bags such as the shape, material and difficulty in placing the bag in the abdomen. The insertion and removal of the bag inside the abdomen requires special skill of usage of the bag by the user and thus requires special techniques to be used as per the design of the bag by the user. Various evidences of spillage of blood and tissue have occurred during morcellation. There are bags having single openings used in the prior art such as in US20040097960, which provides a bag for use in a laparoscopic surgery, having at its one end an opening through which extracted internal organ is put in and drawn from, and having at its other end a tubular organ storage portion with a closed bottom, of which bore diameter is smaller than that of the opening. This invention cannot be used in conjunction with power morcellation.

In US20140236167 to Shibley et al., the cap is placed on the bag mounted to the retractor after the rim of the single port bag is removed out through the incision and the cap is used as an access device for an instrument for morcellation or a surgeon's hand/arm. According to FIG. 24, piercing of the bag is done by trocar to create a port on the bag after the bag is inserted inside the abdomen, in which situation there are high chances of leakage of blood and tissue during removal of the bag from the abdomen. According to FIG. 94, the bag contains a small port with a valve. The disadvantage in such bags is that the location of the port becomes difficult. These bags with small ports can limit the size of tissue to be inserted inside the bag.

In US20140236168 to Shibley et al., the body portion of the bag has a length and width greater than a length and width of the neck portion used for morcellation. FIGS. 160, 161 show creation of the ports during surgery, thereby the chance of leakage is greater in such bags.

In US20130184536 to Shibley et al., the bag has an exit port and an entrance port.

In U.S. Pat. No. 6,752,822, the bag is everted over the severed tissue once the receiving tips have grasped the tissue, and the enclosed tissue and bag may be safely removed from the patient.

However these prior arts have been unable to tackle various issues related to tissue morcellation and insertion in the abdomen and removal of the bag from the abdomen.

SUMMARY OF THE INVENTION

The present invention relates, in general, to the field of biomedical devices used in a surgical procedure and, in particular, to a tissue isolator designed to isolate and extract morcellated tissue while preventing seeding of benign/potentially cancerous tissue during the morcellation procedure.

The present invention provides a tissue isolator comprising two or more openings designed to isolate and extract morcellated tissue during a laparoscopic morcellation procedure wherein present invention is so designed to suit any number of abdominal port preparation/usage during laparoscopic surgery using the tissue isolator for isolation and extraction of morcellated tissue. Thus, the user does not have to create any opening during the procedure. This further limits leakage and the opening may be closed as per requirement by the user. The present isolator allows larger tissues to be inserted into it. It also prevents spillage during tissue morcellation and facilitates insertion in the abdomen and removal of the isolator from the abdomen.

In an embodiment the tissue isolator is made of specific shape to enhance the usability and utility of the tissue isolator during the surgical procedure. Various markings for identification and positioning of isolator inside the peritoneum to further enhance the usability of the isolator are also disclosed.

In an embodiment the isolator optionally comprises at least one sealing element to seal the isolator during use.

In an embodiment the isolator optionally comprises at least one closure element to close the isolator after use and before removing it from the patient body.

The tissue isolator provides a method of isolating and extracting tissue from the body.

In an embodiment, introducer is disclosed which can be used to assist the user in using the said isolator.

In an embodiment, a deployer is provided to assist the user in using the said isolator.

The foregoing objects and other advantages and features of the invention may now be more readily ascertained from the following detailed description of a preferred embodiment thereof, taken in conjunction with the accompanying drawings.

DESCRIPTION OF THE INVENTION

The description below provides various embodiments of the tissue isolator of the present invention and use thereof.

Figure 1:
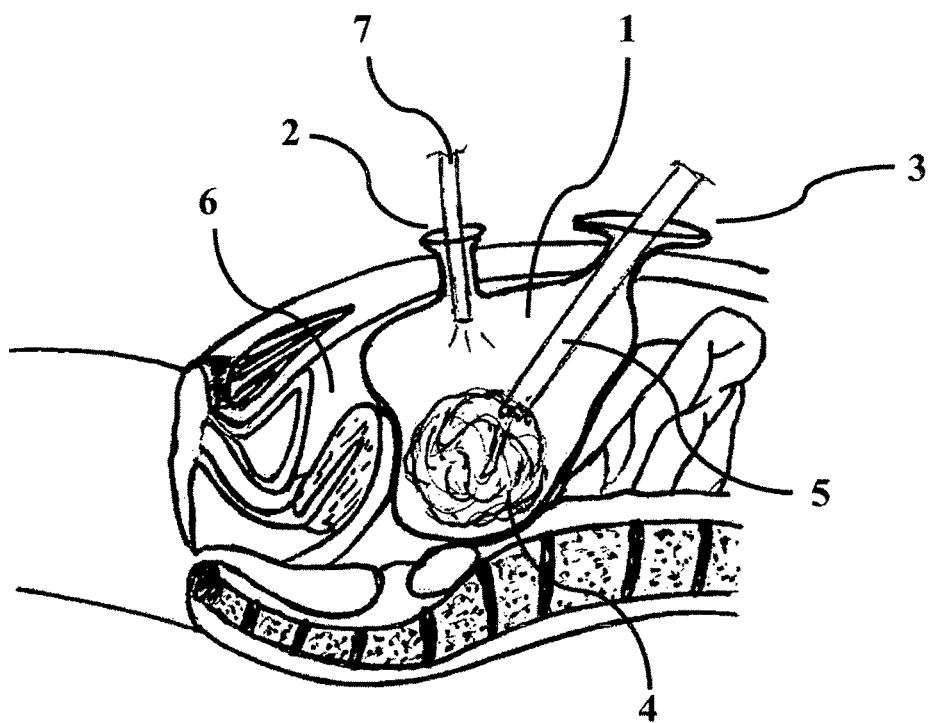
FIGS. 1 to 3 illustrate a tissue isolator of the present invention.
Figure 2:
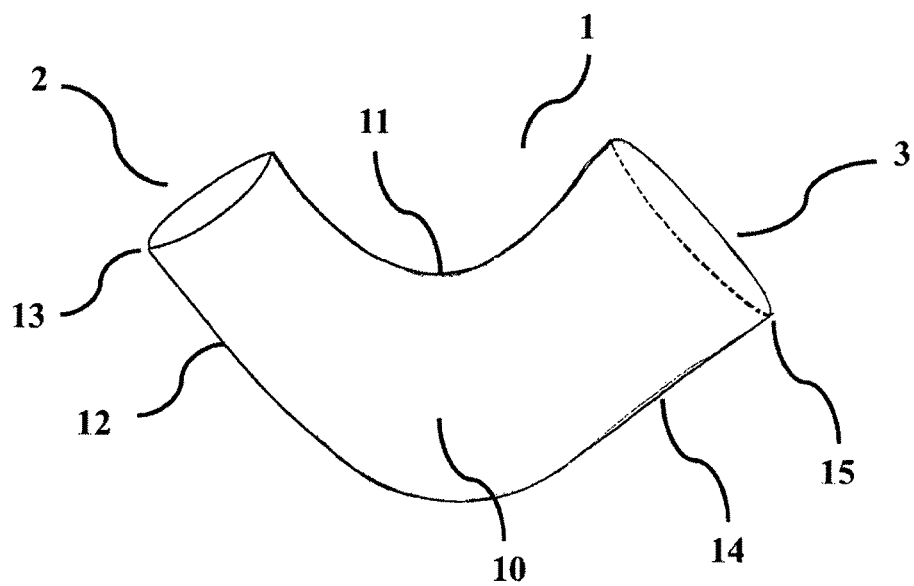
Figure 3:
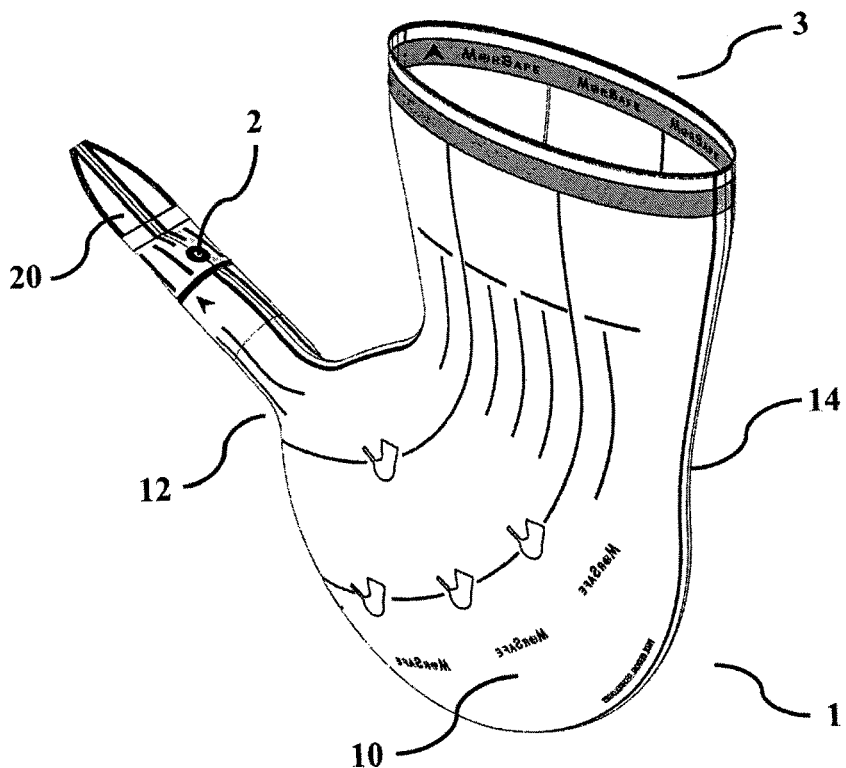

The present invention provides a tissue isolator designed for isolation and extraction of morcellated tissue during a surgical procedure such as a laparoscopic procedure. Referring to FIGS. 1, 2 and 3, a tissue isolator 1 of the present invention is provided, which is biocompatible and comprising two or more openings 2, 3 designed to prevent dissemination of potentially cancerous tissue during morcellation or surgery. FIG. 1 shows the isolator 1 inside the abdomen with openings 2, 3 with tissue 4 placed inside the isolator. The said isolator 1 is biocompatible for safe use during surgery. The isolator 1 has two or more openings 2, 3 and can be suitable for use with any number of abdominal port preparation/usage during laparoscopic surgery.

An opening is a lumen, which extends outwards and which allows access to the interior space of the isolator. A port is a self-sealing structure to prevent fluid loss from the pressurized body. FIG. 2 describes the isolator with at least two openings. In the said isolator, a central body portion 10 forming an interior space configured to receive a tissue, said central body portion having a top section 11. Further a neck 12 integrally formed with said central body portion, said neck having a proximal end extending outward from the said top section of said central body portion and a distal end 13. An opening 2 formed at the distal end of said neck, said opening and said neck configured to receive a first surgical instrument or tissue. Further the said isolator comprises of a neck 14 integrally formed with said central body portion, said neck having a proximal end extending outward from the said top section of said central body portion and a distal end 15. An opening 3 formed at the distal end of said neck, said opening and said neck configured to receive the tissue or instrument.

In one of the embodiments shown in FIG. 3 opening 3 and neck 14 are substantially larger than opening 2 and neck 12. Further the openings may be located toward the top section 11 or on the upper side prevent spillage since both openings are located higher than the central body portion 10. Further one of the opening 2 is small enough that it seals itself on the instrument to avoid gas leakage once an instrument passes through it.

In another embodiment as shown in FIG. 3, the diameter of opening 3 may be larger than neck 14 of the isolator 1, so that tissue can be easily inserted into it. Once inserted, when the user pulls the opening out of the abdominal port, the tissue may easily slip through its neck 14 section and pass into the central body portion 10 due to flexibility of the material of construction.

When a tissue collection bag, disclosed in the prior art, is punctured to provide an additional port, it creates a risk for tissue spillage. Hence in the isolator 1 of the present invention, a second opening is provided prior to insertion into the body and can be completely brought out of the body. Thus, the tissue is completely isolated.

In one of the embodiments, the opening 2 can be in the range of 1 to 50 mm in diameter to accommodate various size instruments. The opening 3 can be in the range of 30 to 300 mm in diameter to accommodate the tissue of 20 to 300 mm diameter. The connecting neck can be either of similar size to its opening or it can be smaller than the opening e.g, neck size can be 2% to 50% smaller than the opening. A higher opening to neck ratio can prevent the isolator from slipping back into the abdomen once the opening is taken out of the abdomen. The neck 12 or 14 may have sudden bulge to avoid wrinkles at that section when isolator is inflated. Any one of the openings is used for the passage of trocar through it, so that laparoscope 7 (FIG. 1) can pass through the trocar and seals the opening section. The other opening can be used to accept power morcellator 5 (FIG. 1). The central body portion of the isolator may have volume in the range of from 300 ml to 8000 ml. When the trocar passes through the opening 2, due to its elastic property, it can stretch and allow the trocar to pass through it by sealing around it. This can provide a natural sealing around the trocar, thereby preventing gas leakage from around the trocar. This also minimizes crumpled material around the port and enables good visualization. Further optionally, the tail 20 of the isolator 1, as represented in FIG. 3, is made in such a way that user can hold the tail 20 while insertion of the trocar through it.

The bags described in the prior art, have a single opening and a rectangular or conical shape. During surgery, the rectangular shaped bags have more material to be inserted inside the abdomen. Thus after insertion of such bags inside the abdomen, when inflated the bag tries to take its natural rectangular shape, but due to the natural sphere like shape of the abdomen, the ends of the bag try to accumulate at its corners. This accumulated material of the bag may cause difficulties in morcellation such as occluded vision, twisting and such like.

Figure 4:
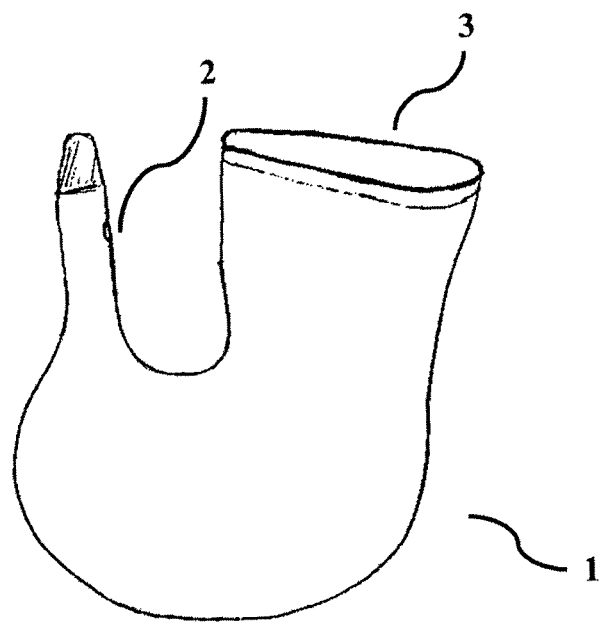
FIGS. 4 to 6 illustrate various embodiments of the tissue isolator of the present invention.
Figure 5:
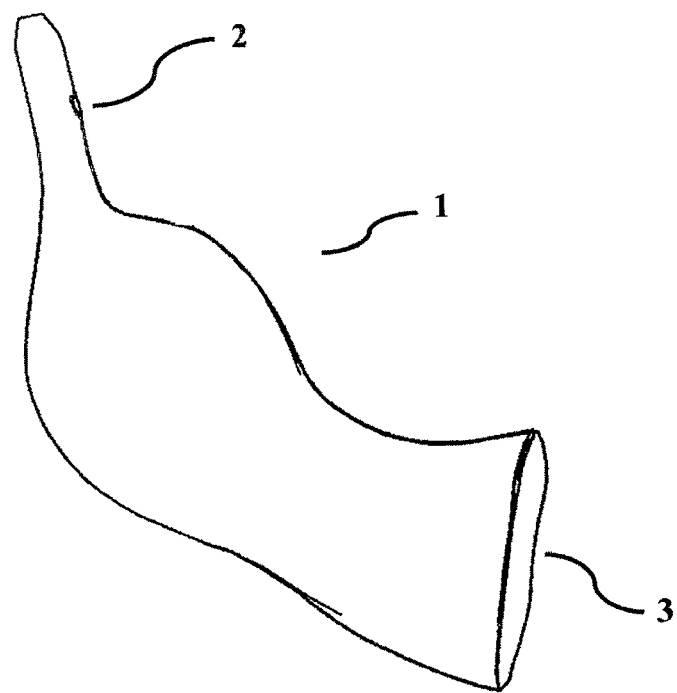
Figure 6:
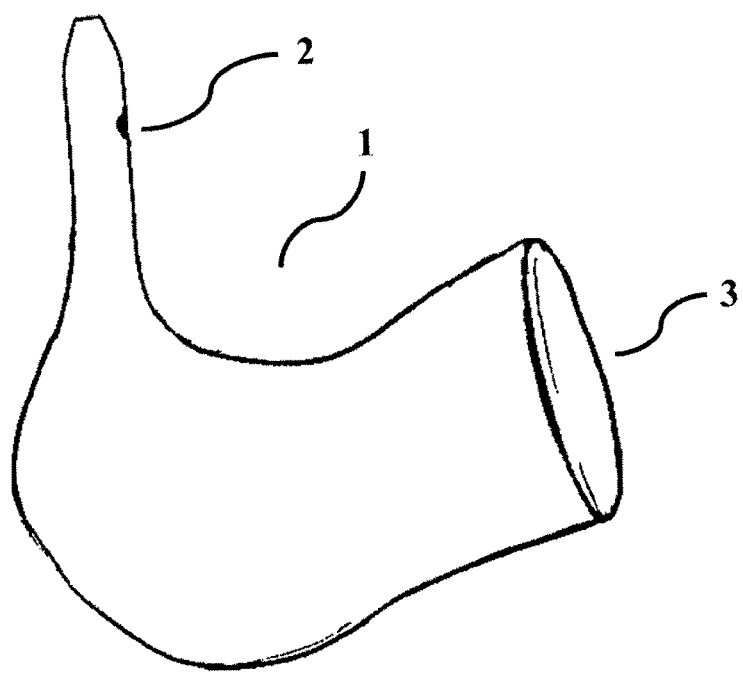

Thus to overcome these issues the isolator is made in unique and innovative shapes like being substantially curved as shown in FIG. 3, U shape as shown in FIG. 4 or L shape as shown in FIG. 5 or J Shape as shown in FIG. 6. The U shape is provided to suit the morcellation through umbilicus port and suprapubic port. One opening may come out of the suprapubic port and the other opening may come out through the umbilicus port. The L shape as shown in FIG. 5 and J shape as shown in FIG. 6 are made for port positions at the sides of the abdomen, where one opening may come out of the umbilicus port and the other opening may come out of the left or right side port.

The central body portion when inflated is made to contain tissue for morcellation. The central body portion is designed to conform to the shape of the inflated abdomen. Further, the central body portion is made in the disclosed unique shape to easily accommodate different tissue sizes. If the isolator is made in a straight tubular shape, the tissue may slip out of the other opening when the one of the openings is pulled out. The unique shape provided prevents the tissue from slipping out of the opening.

Figure 7:
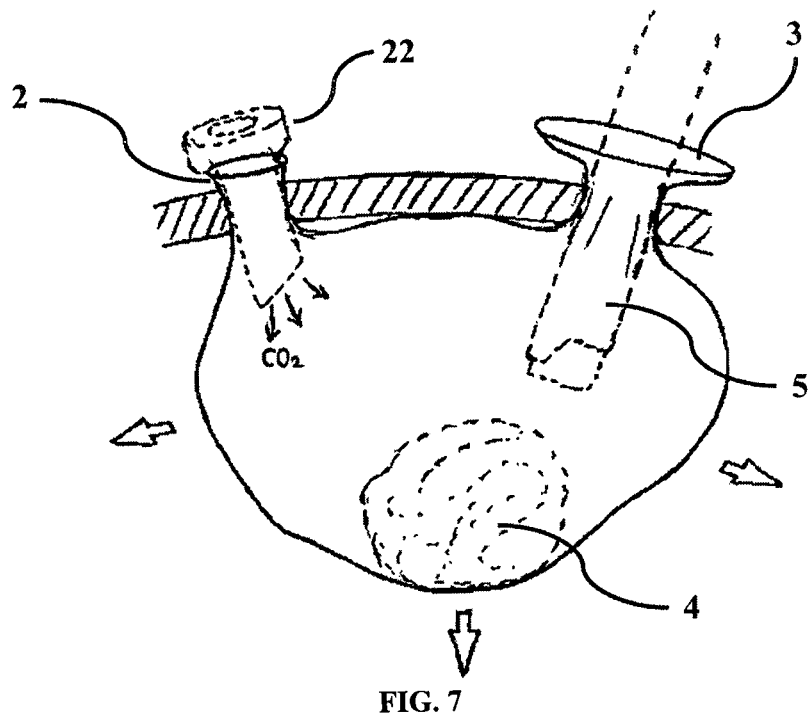
FIG. 7 illustrates an inflated isolator.

FIG. 7 shows the inflated isolator 1 in the abdomen. Power morcellator 5 is inserted through one of the openings, preferably the opening 3. Trocar 22 is inserted through the other opening, preferably the opening 2.

Figure 8:
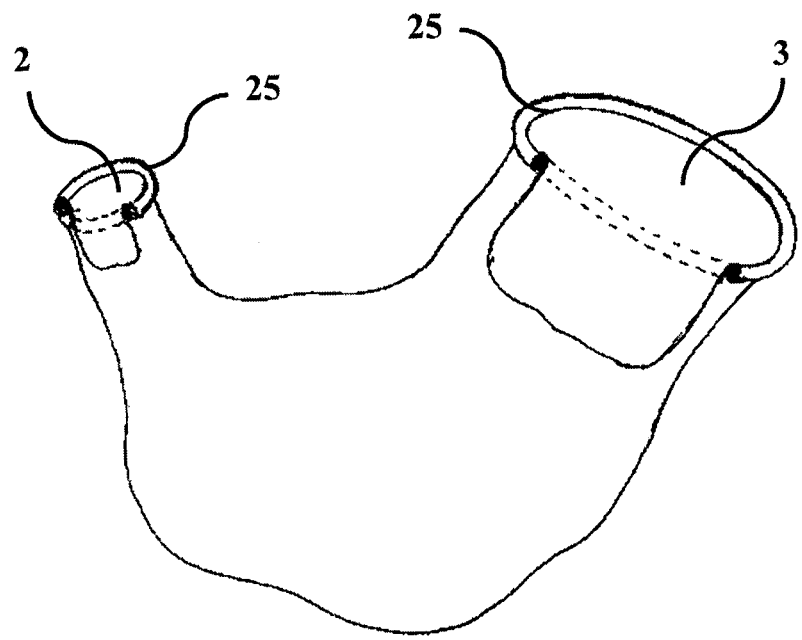
FIGS. 8 to 11 illustrate flexible element of the tissue isolator of the present invention.
Figure 9:
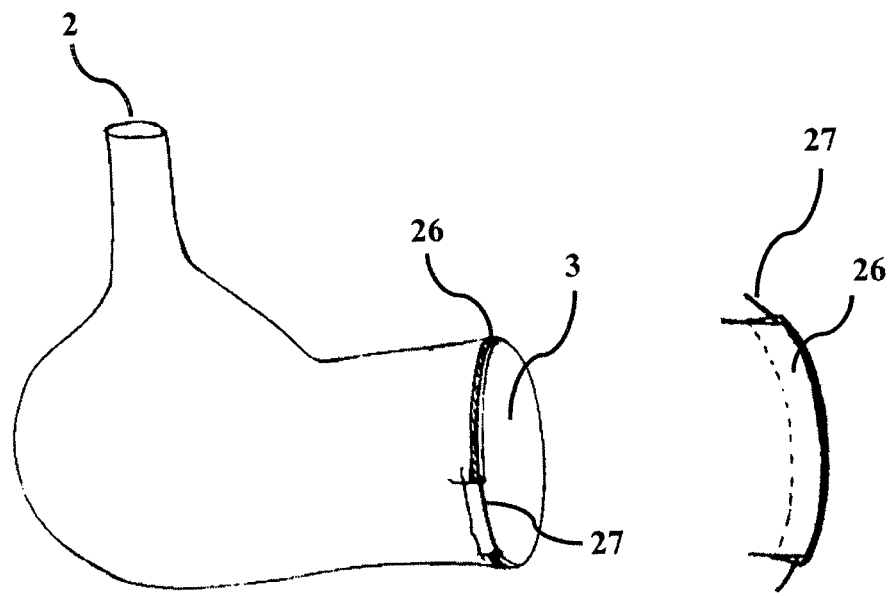
Figure 10:
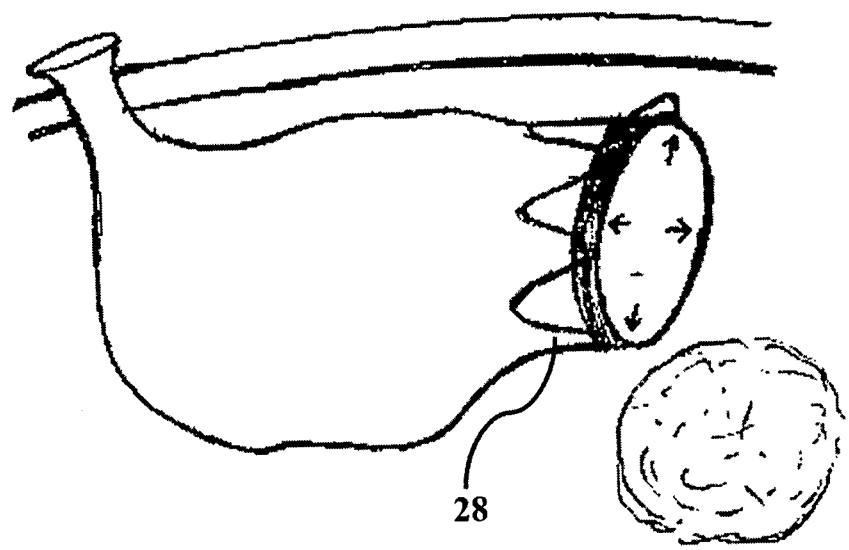

Another disadvantage of prior art is that during surgery, the surgeon may be unable to easily separate the two surfaces of the opening to insert tissue through it. The two surfaces may stick to the tissue and create difficulty in insertion of tissue into the isolator. To overcome this problem, in accordance with one of the preferred embodiment of the invention, to make the tissue insertion inside the isolator easier, any or all of the openings 2, 3 of the isolator can open itself after entering inside the abdomen. As shown in FIG. 8, the openings 2, 3 may optionally include a flexible element. The flexible element can be an integral part of the opening or an elastomeric ring 25 attached to the opening. In preferred embodiment, as shown in FIG. 9, the flexible element may be a wire or loop 27 made of super elastic material such as nitinol, to reduce the amount of material, and may be attached to the opening 3. The said wire may be attached by passing through the tubular pocket 26 created at the opening of the isolator. The flexible element can be deformed to any shape but once released takes its natural shape. The flexible element 25 and 27 as shown in FIG. 8 and FIG. 9 respectively will preferably have a cross-section in the approximate range of 0.1 mm to 10 mm in diameter. As shown in FIG. 9, the flexible element 27 may be enclosed in a tubular pocket 26 provided at the opening, so that flexible element 27 will not be exposed. The tubular pocket 26 can be created by folding the distal end of the opening back downward and fastening it to the isolator 1 such as by sewing, heat sealing or the like. According to an embodiment of the invention as illustrated by FIG. 10, the opening may have nitinol or spring steel wire formed in zig-zag form 28 that is positioned at the opening. In a relaxed condition, it is opened by its shape memory or flexible characteristic and it can be compressed.

Figure 11:
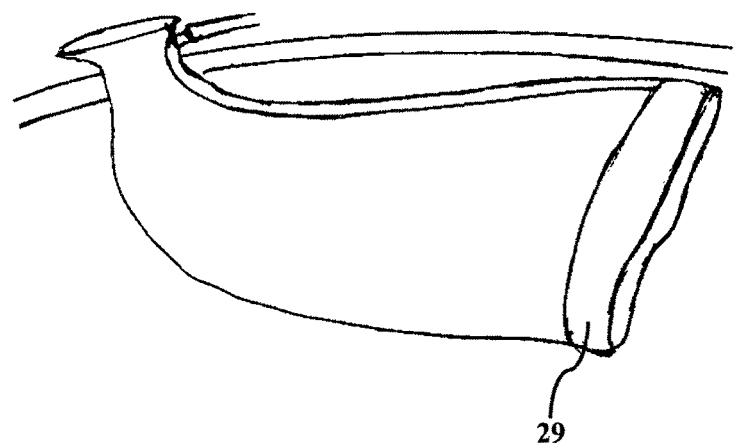

In another embodiment as shown in FIG. 11, the flexible element may be in the form of inflatable ring 29. The action of opening of the isolator may be made easy by having an inflatable ring 29 around the opening of the isolator. The said inflatable ring can be inflated from outside by pumping in air or liquid. Inflation of the ring can open the opening of the isolator to facilitate tissue insertion by the surgeon.

According to an embodiment of the invention, magnetic strips may be embedded within the opening of the isolator. There can be two or more strips with same polarity embedded facing one another. As both edges of the opening come closer to each other; due to repulsion the edges of the opening will repel each other and will remain open. Thus after inserting isolator inside the inflated abdomen, the opening of the isolator opens itself.

In prior art, the inventions provided do not have appropriate markings to guide the user during different procedures of morcellation. Since the isolator is transparent, semi-transparent or opaque, the user may find it difficult to distinguish between the isolator and tissue or different sides of the isolator or edge of the isolator. Further it may take more time to locate the openings of the isolator. While inserting the tissue inside the isolator, the user may be confused between the inner and outer side of the isolator. Even during insertion of trocar through one of the opening, it may be difficult to locate the opening and thus user can puncture hole at any undesirable location at opening. To make the isolator easy to use and also save procedural time, the isolator may be made in various colors or markings. Further to reduce chances of user error, markings may be provided on the isolator.

Figure 12:
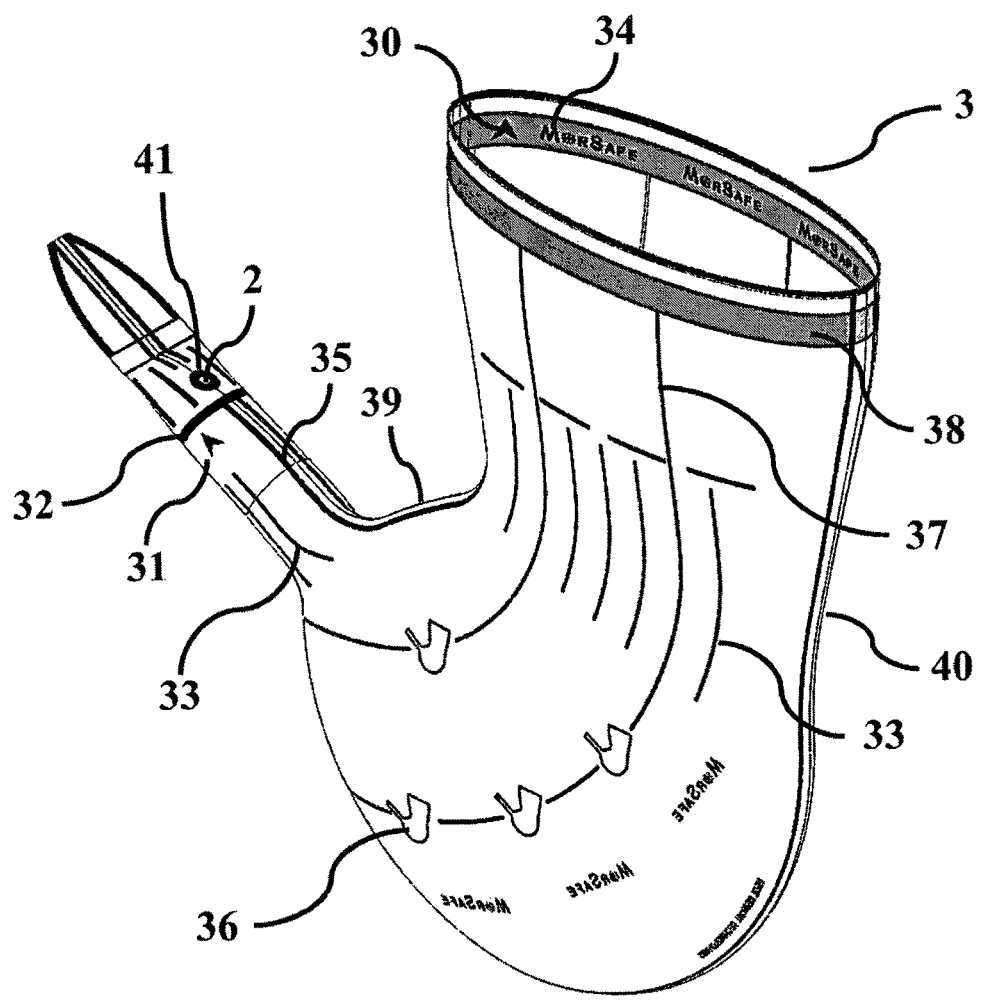
FIGS. 12 to 13 illustrate an identification mark on the tissue isolator of the present invention.

Some of the representative markings are disclosed herein. In an embodiment as shown in FIG. 12, arrow markings 30 may be provided on the upper side or end of the opening 3. The arrow mark may be visible from inside as well as outside of the isolator. This marking indicates grasping location while pulling out the opening 3 through the abdominal port. Arrow marking 31 is an indication of the opening 2. Line 32, preferably thick, at opening indicates the location for knot formation or placement of closure element, provided below in the disclosure. There may be vertical lines 33 on the neck portion of the openings which indicate any twisting of the isolator at the opening, i.e. the surgeon will be aware of twisting while pulling out both ends of isolator through their respective abdominal ports. There may be prints 34 on the band 38 wherein the band 38 can be colored such as blue color. These prints are to indicate the inner side of the isolator at the opening and differentiate it from the outside of the isolator. In one embodiment, the print is visible only from the inside of the isolator and not from the outside. This helps the user to easily identify the inner side of the isolator, while inserting tissue inside the isolator. Lining 35 is provided preferably on the shorter edge 39 of the isolator to distinguish it from the longer edge 40 of the isolator. There may be directional markings 36 to indicate the direction of the openings. These directional markings 36 may be an arrow shaped or of representative shape of the isolator itself. This helps the surgeon to locate the openings of the isolator after insertion of the isolator inside the abdomen and while viewing with a laparoscope. A colored filled or unfilled circle 41 can be provided around the opening 2 wherein this marking may help in easy identification of the opening of the isolator while insertion of the trocar through it. Marking 37 may run across the length of the isolator body. Such marking may help the user to distinguish the isolator body inside the abdomen from surrounding tissue 6 (FIG. 1).

Figure 13:
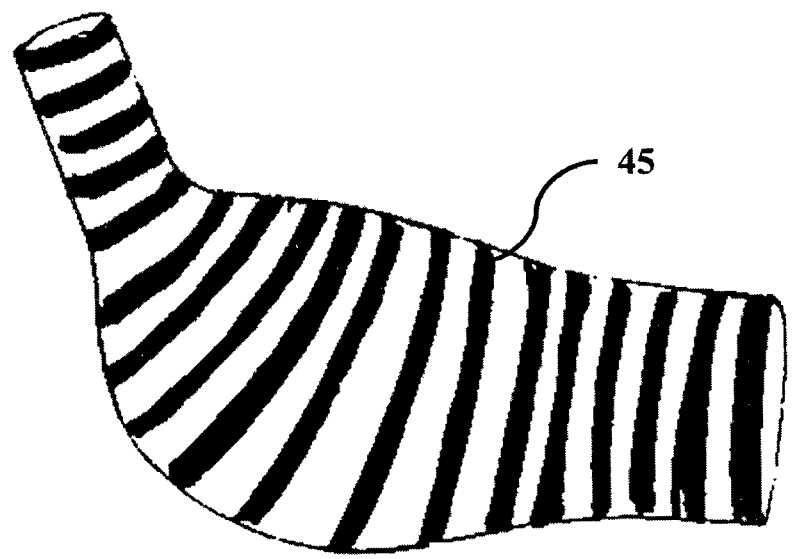

In accordance to yet another embodiment of the invention, the isolator may be colored, opaque or transparent; there may be marking/indicators. This color indicator/marking will help the user in easy identification of the opening inside the abdomen. There may be any colored arrows or markings for indication of positioning and to prevent twisting. There may be colored lining on the isolator openings, it may be any color such as blue, green or the device may have outer and inner surface in two different colors such as outer surface in light blue and inner surface in light green or the isolator outer surface may have a plurality of colored lines that extend circumferentially around the entire isolator parallel to one another like zebra lining 45 or in any other pattern as shown in FIG. 13.

In the preferred embodiment, the isolator may be made from thin elastic film such as Thermoplastic Polyurethane with thickness in the preferable range of 10 to 500 microns. This material should be thin that it can be easily placed in the introducer or can be passed through the 10-30 mm abdominal port. This material can possess high strength and can be stretchable. Thus even if sharp devices press against the film, it can resist rupture to a great extent. Due to this strength and elasticity, the chances of the isolator getting ruptured are minimized.

In yet another embodiment, the isolator may be made of material such as Nylon thin film, which can provide strength to the isolator making it cut resistant. The isolator may also be made from one or more layers of similar or dis-similar materials or a composite material to prevent tearing and better performance of the device during its use in the procedure.

Surface finish of the isolator may be matted, to avoid reflection of light. In one of the embodiment, the surface of the isolator may be coated with anti-microbial coating or nano-silver coating.

According to another embodiment of the invention, the isolator may be made from any of the cut resistant woven or non-woven material like CARBON FIBER, GLASS FIBER, KEVLAR®, SPECTRA®, Cut-Tex® PRO, ATA, Dyneema, TWARON®, HexArmor® etc, and elastomeric or plastic coating may be done on one or both side to fill invisible pores, so that no fluid can come out from the isolator. The isolator can achieve flexibility and can be expandable to take the area of the abdomen or peritoneum. Also, morcellator or any instrument cannot cut the inflated isolator during insertion of the morcellator or such instruments and while morcellating or cutting the tissue. The isolator can thus achieve cut resistant properties with flexibility.

In yet another embodiment of the invention, the isolator may be made in at least two layers, where inner layer is made of cut resistant woven material and outer layer is made anti leak layer from any of these materials such as thin plastic or elastomer like PU, silicone, nitrile. Both the layers may be joined to each other.

In accordance with yet another embodiment of the invention, the isolator may be made of composite material wherein the inside layer is made of mesh (e.g. nitinol, steel or any strong material etc.), which is resistant to cutting from sharp objects or instruments. The pore size of the mesh can be carefully selected so that the smallest arc of the cutter tip does not penetrate through the mesh. The mesh can be covered by a thin elastic membrane to avoid leakage of the tissues or blood. Further the mesh should keep the isolator supple and flexible during its introduction and removal from the abdominal cavity.

Figure 14:
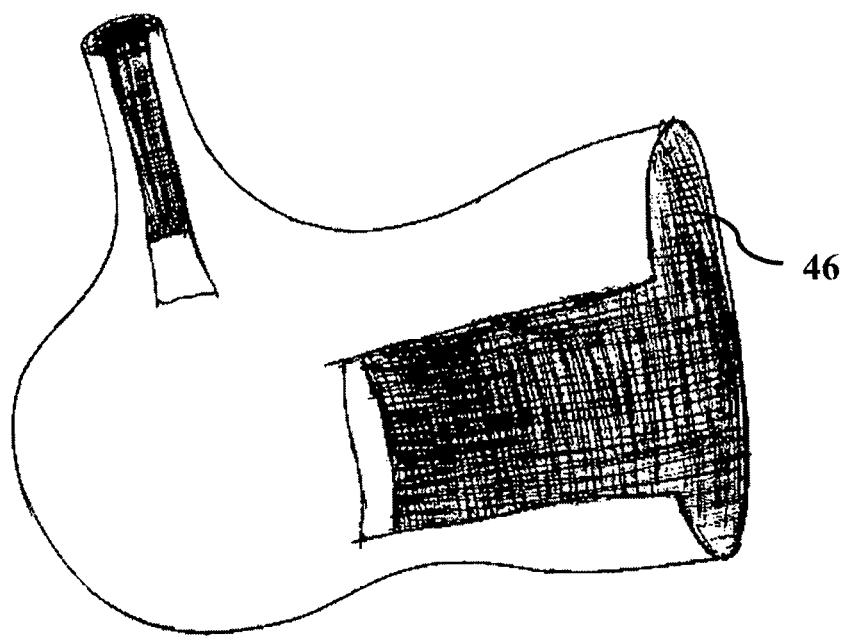
FIG. 14 illustrates a one or more layer structure of the tissue isolator of the present invention.

In accordance with yet another embodiment of the invention, the isolator may be made by attaching rip-stop lining 46 at one or both the openings up to the neck section of the isolator as illustrated in FIG. 14. This rip-stop lining 46 at the inner side helps in avoiding cut or tear of isolator during use of sharp instruments (e.g. trocar) through it. The rip-stop lining 46 may be made from Nylon or any suitable material that resists tearing.

In another embodiment, the inner layer of the isolator may be made from slippery material or it may have a coating of slippery material. The slippery material can be lubricious or hydrophilic or hydrophobic or gel. The coefficient of friction ($\mu$) of hydrophilic coatings may range from 0.01 to 0.3. The inner layer may also be so slippery so as to prevent the sharp instrument from cutting the isolator. Further the slippery material may help to place the tissue with ease into the isolator. Further, it may help in free rotation of the tissue during morcellation or cutting inside the isolator.

In accordance with yet another embodiment of the invention, the isolator can be made of more than one layer of membrane. A liquid or gel material may be filled in between at least two layers. In case the layer is cut, the fluid can spill out indicating the user to stop or change the plan of surgery. In one of the variations, the inner layer may be opaque white and the fluid/gel may be blue or any other color so that as soon as the layer is cut, it can give a visual indication of the cut. In accordance with yet another embodiment of the invention, the isolator can be made of alternate variable thickness material with first thickness region and second thickness region. Thick section can provide strength and shape to the isolator.

Figure 15:
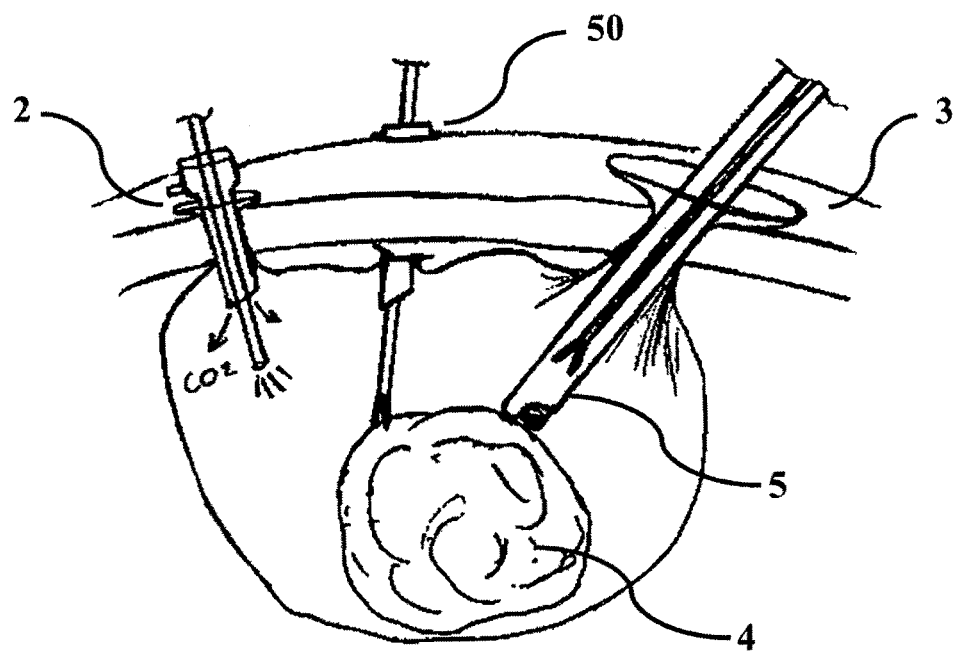
FIGS. 15 to 20 illustrate variants of two or more openings of the tissue isolator of the present invention.
Figure 16:
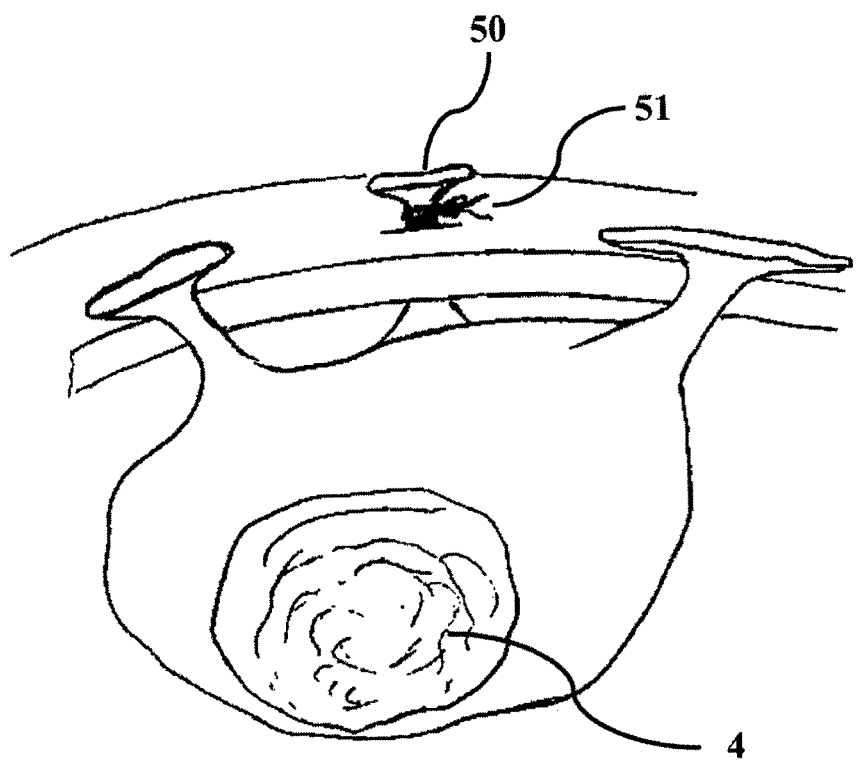
Figure 17:
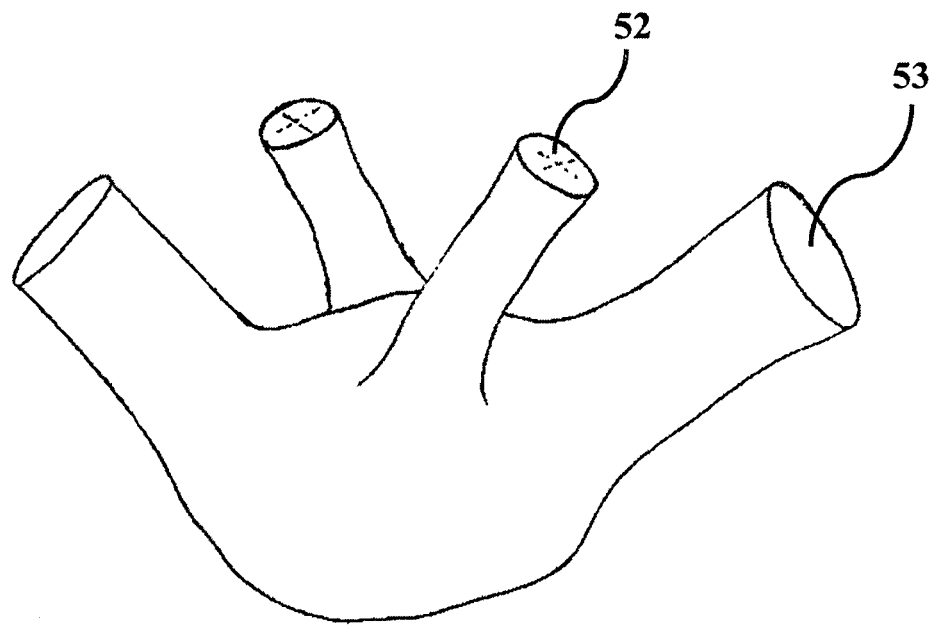

In accordance with yet another embodiment of the invention, the isolator may have two or more openings as shown in FIG. 15, FIG. 16 and FIG. 17. In one of the embodiment one of the openings 50 will be along the top section and rest of the openings will be on the top section or on the upper side of the isolator. After placement of tissue 4 inside the isolator, any or all the openings may be exteriorized from the incisions on the abdomen. All or any one of these openings may be sealed by trocar, through which grasper or laparoscope can be passed. Trocar may be used to pass gas inside the isolator to inflate it.

Figure 28:
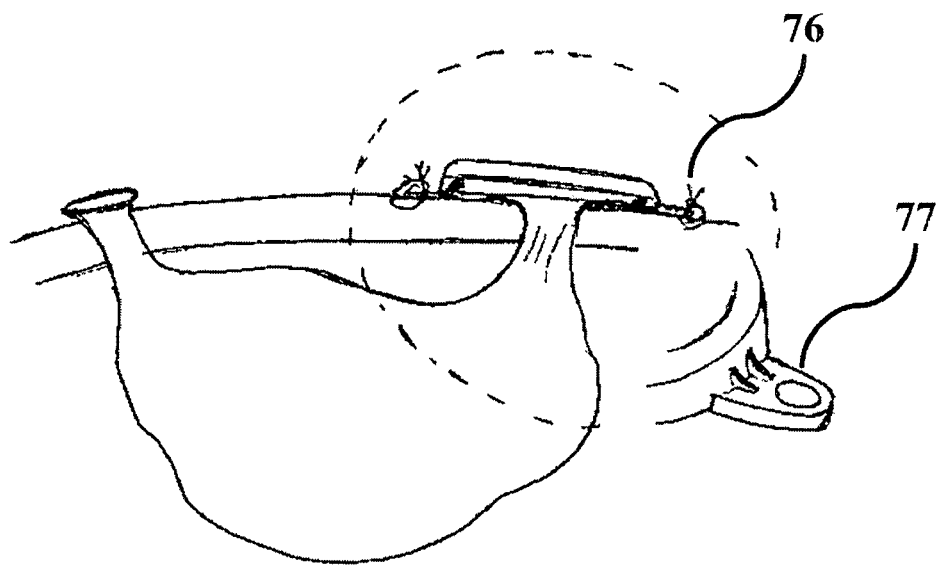

In one embodiment of the invention, shown in FIG. 16, the isolator may also be used having two or more openings. All or any of the openings (except for the openings being used) can be closed by purse string 51 or a closure element such as the one shown and described in FIG. 35 or closed in various other ways and can be opened by the user as and when needed. All the openings coming out of the abdominal ports may be held in place by the friction between isolator neck section and abdominal wall. Alternatively the opening can be tied by sutures to the outer abdominal wall with the help of structure 77 as shown in FIG. 28.

Figure 18:
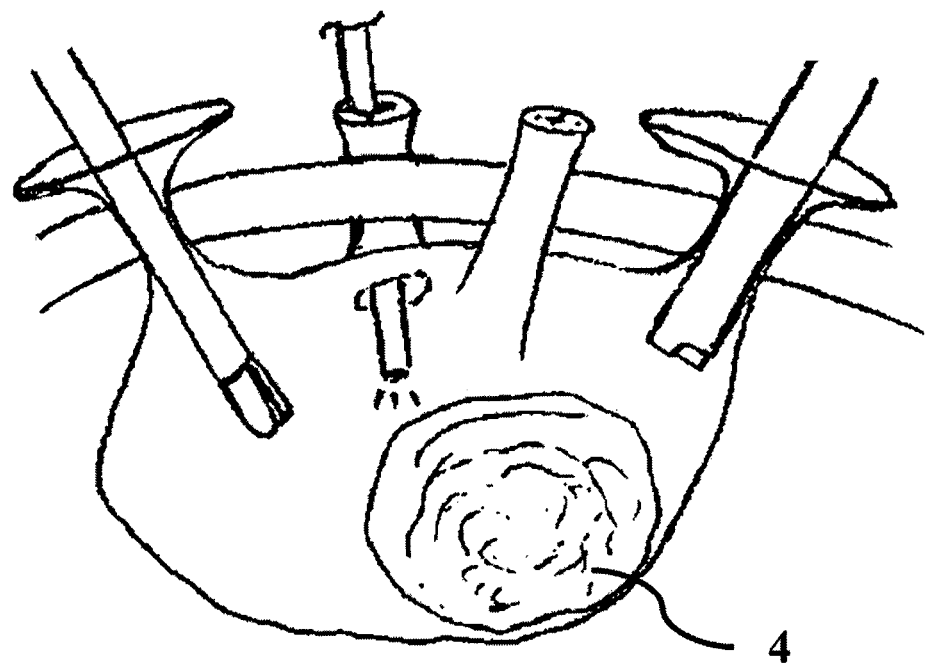
Figure 19:
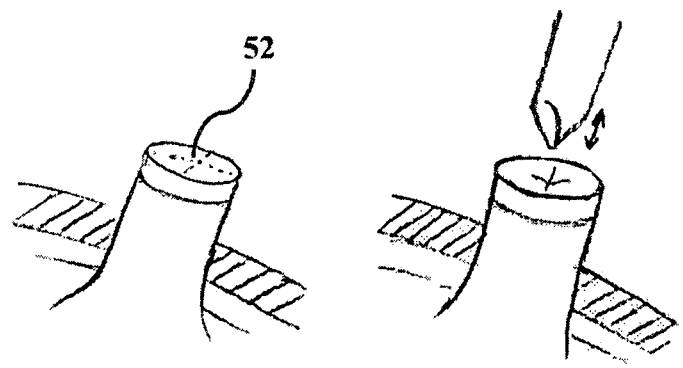
Figure 20:
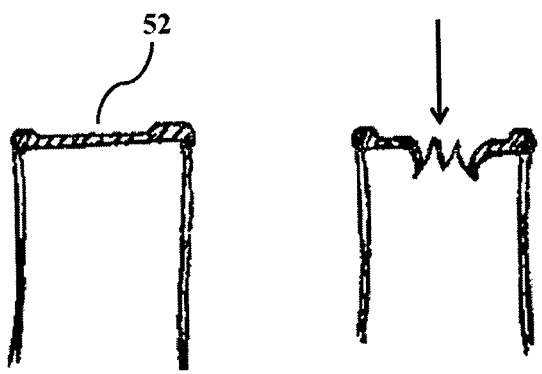

In another embodiment of the invention, shown in FIG. 17, some openings may optionally be in a closed state 52 while other openings may be in open state 53 or all openings may optionally be in closed state 52. The open state openings can be used to place the tissue into the isolator. The closed state opening may be used when instruments such as laparoscopic graspers or morcellator needs to be passed to aid in the morcellation procedure. As illustrated in FIG. 18, FIG. 19 and FIG. 20, instrument such as piercing tools can create an incision in the closed opening so that the required instrument can pass through it. On passage of the instrument, the incision may create a leak-proof seal around the periphery of the instrument due to material property of the isolator. After completion of tissue morcellation, those openings may be closed by purse string or a closure element to lock it, so that tissue or blood or fluid does not leak out during removal of isolator. In another embodiment of the invention, the unused closed openings may be left inside the abdomen during surgery.

In yet another embodiment of the invention, there may be two or more openings placed in an orderly manner or in a random manner. Any of these openings may have sealing element.

Figure 21:
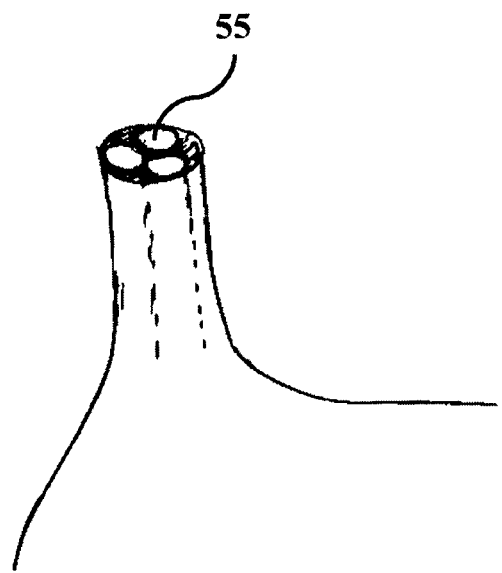
FIGS. 21 and 22 illustrate channels or lumens in the opening of the isolator of the present invention.

In accordance to yet another embodiment of the invention as shown in FIG. 21, the isolator has two or more openings. At least one of the openings optionally includes two or more channels 55 for passage of laparoscopic instruments. All or any of these channels 55 may contain valves for sealing and gas inlet. Alternatively, all or any of the channels may be closed and the user can puncture the closed end to access the central body portion of the isolator.

Figure 22:
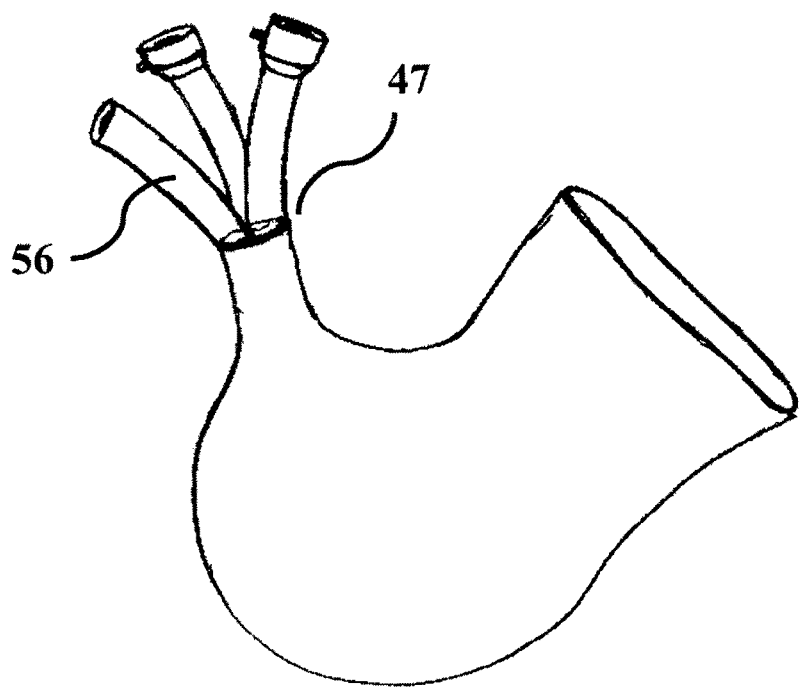

In yet another embodiment of the invention, shown in FIG. 22, at least one opening of the isolator optionally includes multiple extruded channels 56 extending out. The extruded channels 56 help in using the isolator in a single opening laparoscopic surgery with multiple working channels. In similar way there may be multiple extruded channels 56 connected at the edge 47 of the opening to prevent the entanglement of the extruded channels with one another during passage of the isolator into or removal of the isolator from the abdominal cavity.

Figure 23:
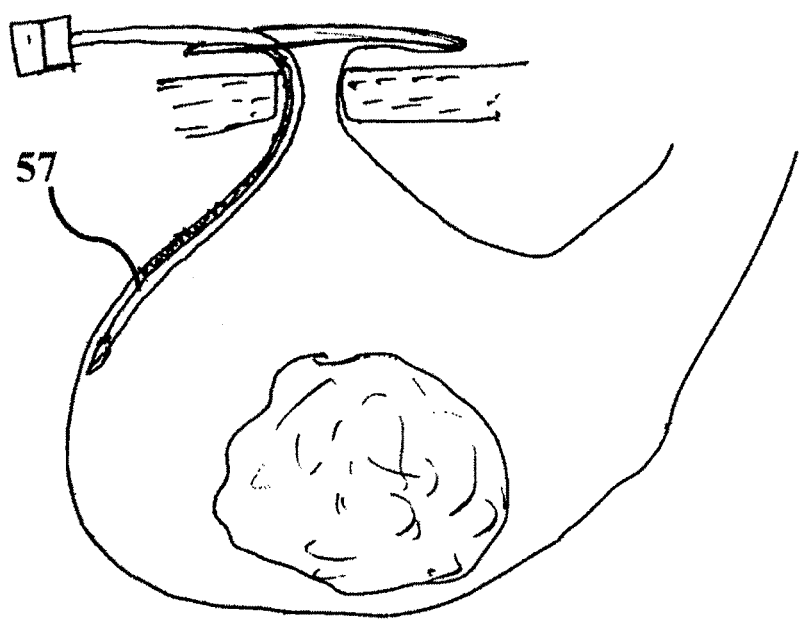
FIGS. 23 and 24 illustrate mechanism to inflate the isolator of the present invention.

The isolator is inserted inside the abdomen and it may be inflated. In an embodiment, a separate tubular structure 57 meant for CO2 or gas passage may be attached to the wall of the isolator as shown in FIG. 23. The tubular structure 57 may be attached to the inner wall of the isolator by methods such as adhesive bonding or heat sealing. The tubular structure 57 may be outside or may be inside the isolator. The tubular structure 57 can be removable from the isolator in one of the embodiments. In yet another embodiment, the tubular structure 57 may be made integral to the isolator.

Figure 24:
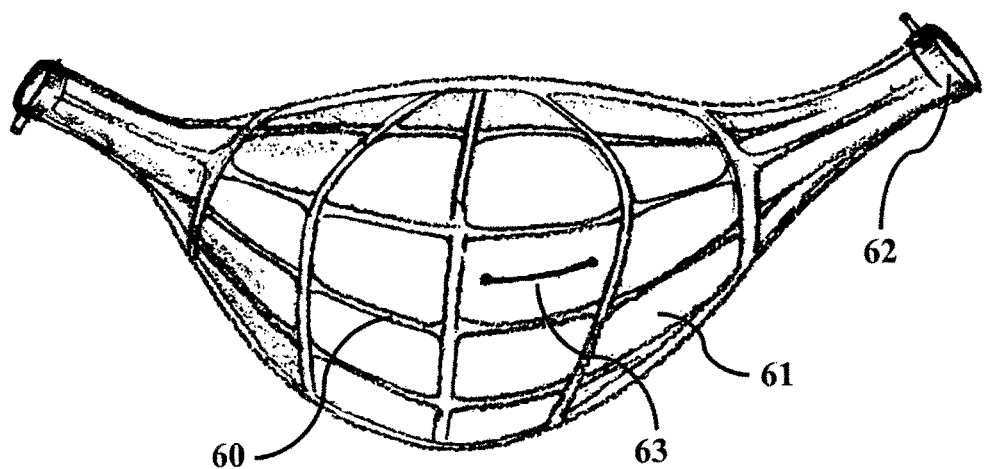

In accordance to yet another embodiment of the invention, illustrated by FIG. 24, the isolator may have a network of tubular channels 60 on its body. All of them are connected to an annular chamber 62 at the openings of the isolator. The annular chamber has a one way valve to retain CO2/gas/fluid inside the tubular channels. The isolator can have water proof elastic or non-elastic sheath 61 between the networks of annular channels to prevent spillage of fluid out of the isolator. Tissue may be placed inside the isolator through one of the openings. Optionally tissue can be placed inside through the flap 63 with or without a valve. This embodiment may not require insufflation of the abdominal cavity as the network of annular channels can provide the required reinforcement and make a clear working area available within the isolator.

In the embodiments described below, the tissue isolator optionally comprises at least one sealing element to seal the opening of the isolator so that the isolator can be inflated in the body. These sealing elements may be in attachable form or releasably attachable or the opening itself may act as seal when morcellator or instruments are passed or when the opening is not in use. Various sealing elements mentioned below may be used together or separately during the procedure.

Figure 25:
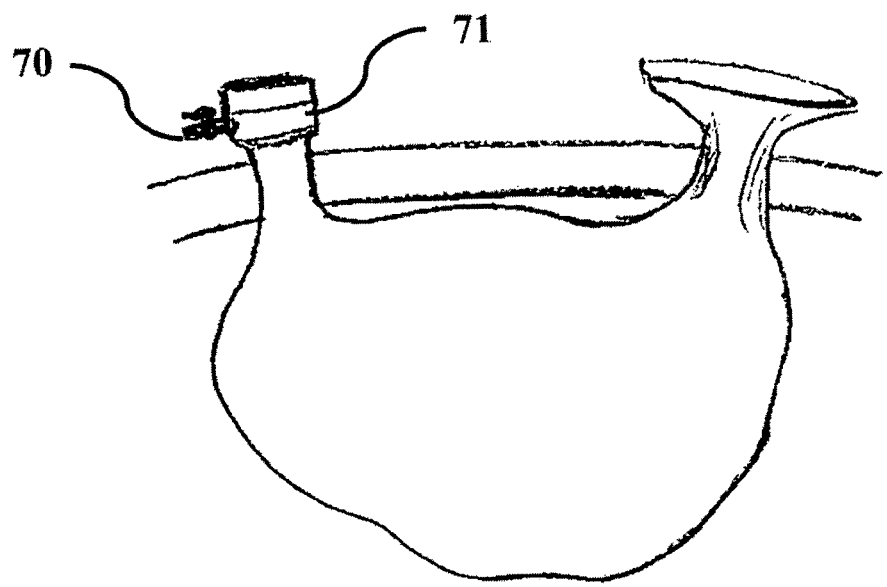
FIGS. 25 to 33 illustrate sealing element used in the present invention.

In another variant embodiment of the invention as shown in FIG. 25, the opening of the isolator may have a pre-attached sealing element 71 such as a sealing valve with insufflation port 70. The sealing valve of the said sealing element can be like the seal valve of a trocar with insufflation port. The embodiment serves a dual purpose of isolator and trocar and hence a separate trocar is not required to be passed through the opening of the isolator.

Figure 26:
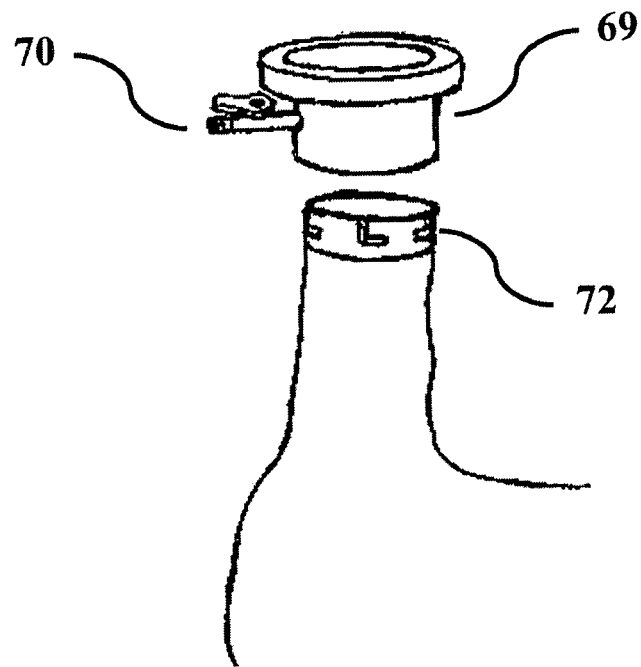

In another embodiment as shown in FIG. 26, the whole sealing element with insufflation port 70 similar to the sealing element 71 (FIG. 25) may be made as reusable and releasably attachable part 69 which can be attached to seal connector 72 by means of different locking mechanisms such as snap lock, twist lock, thread lock.

Figure 27:
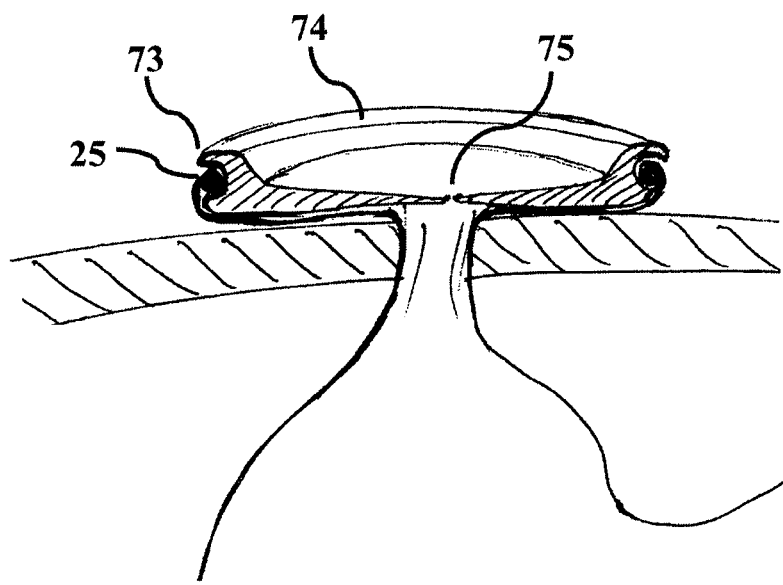

In another embodiment of the invention, shown in FIG. 27, a lock rim 74 may be used as sealing element for locking and sealing the opening on the abdomen. The lock rim 74 may have a curved feature at its edges in which the flexible element such as flexible element 25 (FIG. 8) of the isolator opening can be rolled or wrapped. Thus, the flexible element can be held in the circular hook 73 at the periphery of the lock rim 74. Due to the elastic property of the lock rim 74 the said flexible element can be held in the lock rim. The inner area of the lock rim may have a valve feature 75. The lock rim 74 may be of a size preferably larger than the size of the abdominal port so as to prevent the isolator from sliding into the body. In an embodiment shown in FIG. 28, the lock rim 74 may have at least one tab 77 with hole through which, sutures 76 can be passed to secure the lock rim onto the abdomen.

Figure 29:
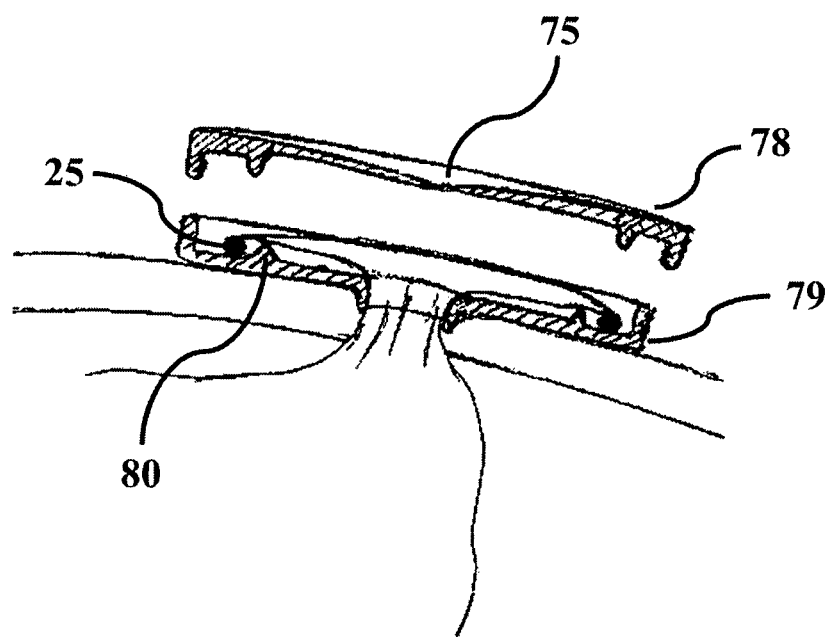
Figure 30:
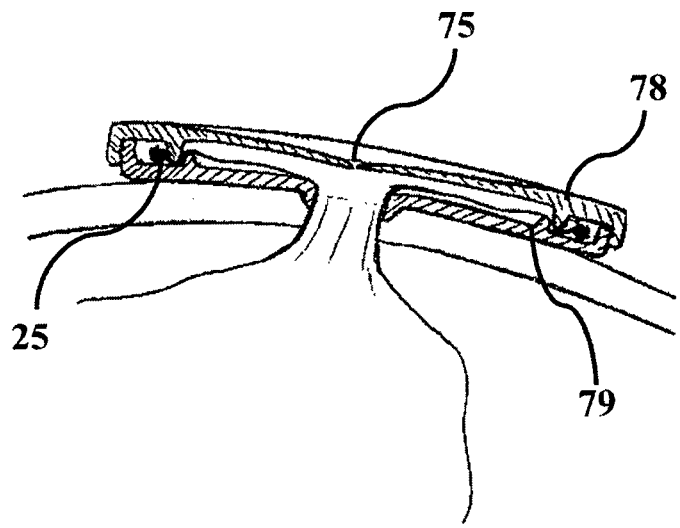

In another embodiment, as shown in FIG. 29, the lock rim may be divided into two parts, upper rim 78 with valve 75 and bottom rim 79. The upper rim 78 and bottom rim 79 can have mating locking features such as threading or snap fit to releasably attach the upper rim 78 with bottom rim 79. The bottom rim can have a holding feature 80 to hold the flexible element of the isolator in place as shown in FIG. 30. The outer periphery of the bottom rim may have features such as the tab 77 with hole, described in FIG. 28, which can be used to fix the rim in its position on the abdomen. The upper rim 78 can be removed to access the abdominal port and it may be attached to bottom rim 79 to seal the abdominal port if the abdominal port is not in use.

Figure 31:
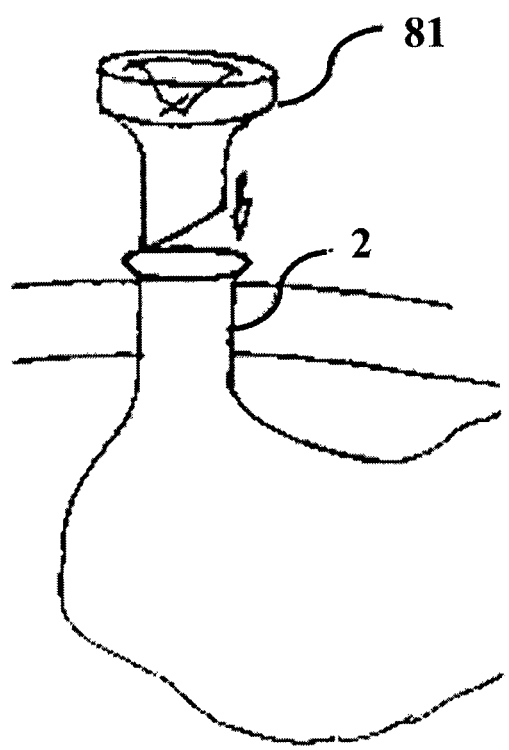

In yet another embodiment of the invention, illustrated by FIG. 31, the isolator opening such as isolator opening 2 can be taken out from an abdominal port and a mini trocar 81 like device or cap with universal seal as sealing element may be releasably attached to the opening of the isolator. This can prevent leak and act as an access port. This mini trocar can be used to provide the passage for the morcellator or for laparoscopic instruments into the isolator in such a manner that the tip of the morcellator or instruments do not come in contact with the isolator thereby preventing any damage to the isolator.

Figure 32:
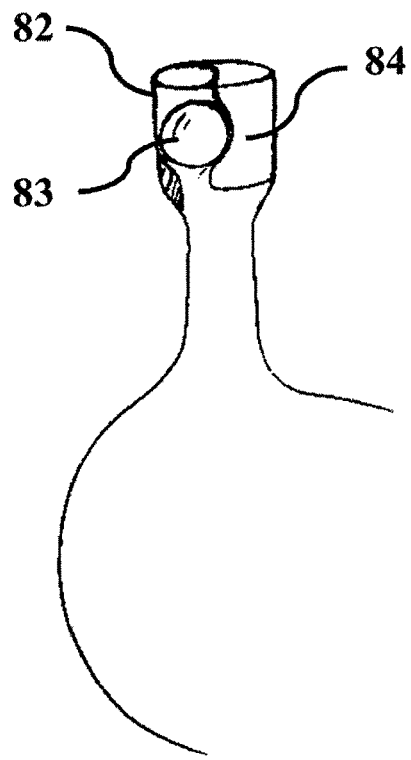

In another embodiment of the invention, shown in FIG. 32, the attached structure 82 at the isolator opening may have metal ball 83 as sealing element and elastomeric pad 84 at its side. The metal ball 83 can seal the opening when there is no device passing through the opening. During insertion of device through the opening, the device can press and move the metal ball 83 to one side by pressing onto the elastomeric pad 84.

Figure 33:
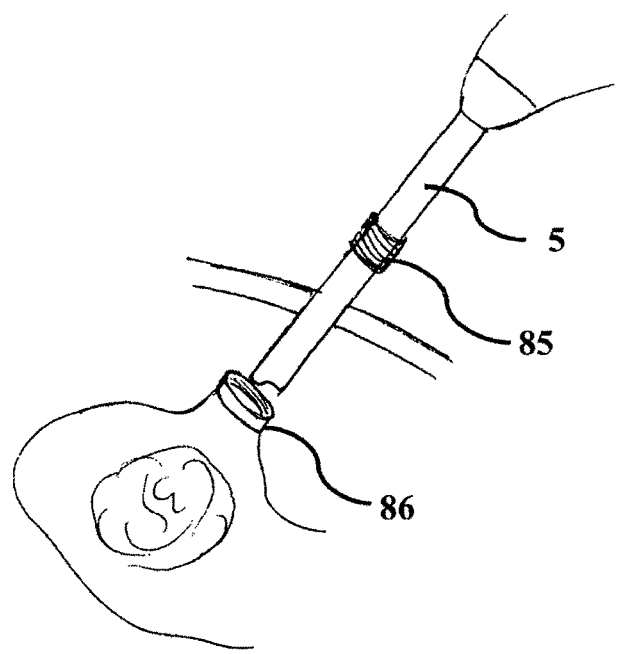

In yet another embodiment of the invention, shown in FIG. 33, the opening of the isolator can have a locking feature 86 such as threading, snap fit that can be releasably locked onto a mating locking feature 85 on the morcellator 5. This can help in avoiding spillage and the isolator need not be outside the body.

In embodiment of the invention described below, the tissue isolator optionally comprises at least one closure element supplied with the isolator to close the opening of the isolator in a leak-proof manner so that the isolator can be safely removed from the body after morcellation is completed. These closure elements may be in attachable form or releasably attachable form or may be movable upwards and/or downwards along the isolator during use or it can be integral part of the isolator itself or it can formed as a procedural step. The following embodiments explain the closure of the isolator using closure element for removal from the body without spillage of blood and tissue after morcellation. Various closure elements mentioned may be used together or separately during the procedure.

Figure 34:
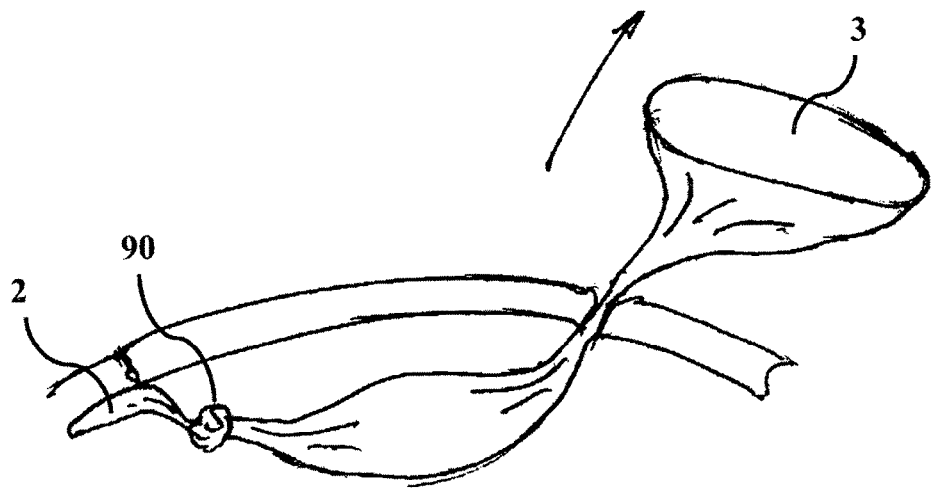
FIGS. 34 to 38 illustrate closure element used in the present invention.

In an embodiment of the invention, illustrated by FIG. 34, one of the openings of the isolator can be tied into the knot 90 acting as a closure element so that it can be removed outside from the body by pulling it as shown in the FIG. 34. The knot 90 may be tied at particular points or at particular identification marks, even above or below any identification mark so that it provides proper closure for the removal. The knot may be tied below line 32 as shown in FIG. 12 for removal of the isolator.

Figure 35:
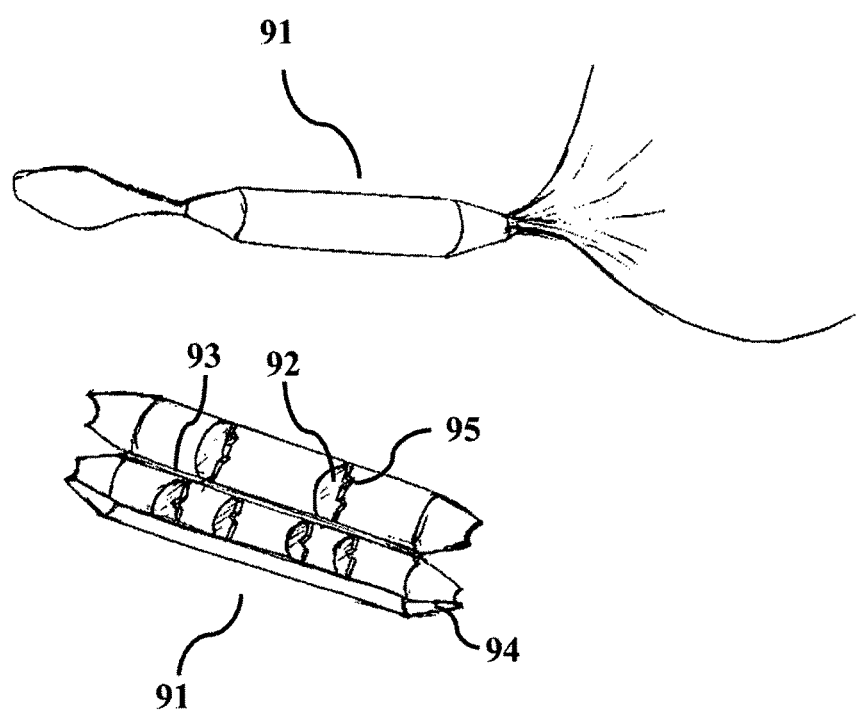
Figure 36:
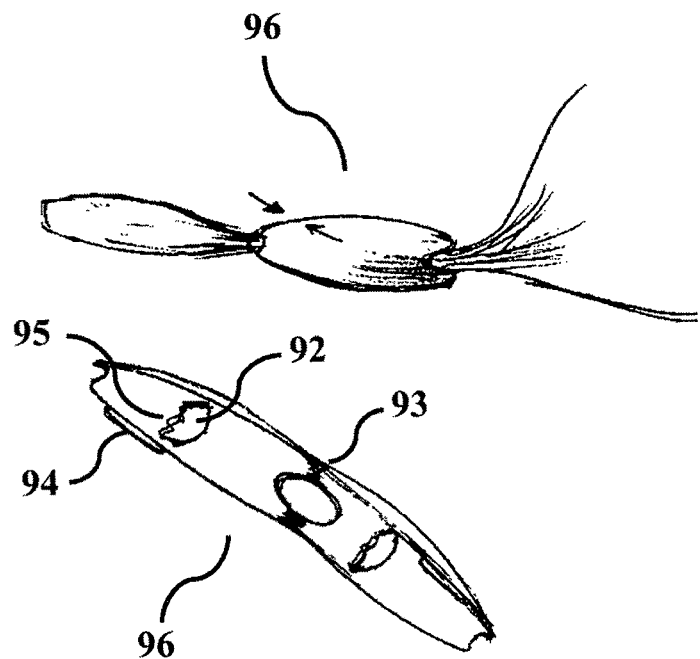

In a preferred embodiment as shown in FIG. 35 and FIG. 36, closure elements 91 or 96 respectively, may be provided as a separate component. After completion of the morcellation procedure, the closure element can be opened, positioned approximately around the opening of the isolator and locked thereby sealing the opening to avoid any kind of fluid leakage.

Closure elements shown in FIG. 35 and FIG. 36, may have at least one rib 92, with optional protruded features 95 to press onto the isolator and completely close the area above and below the opening thereby preventing any fluid from coming out of the opening. The closure elements can further have locking snap 94 to hold the closure element in locked position. The two sections of the closure element may be connected by living hinge 93. The closure element may be open from both the ends, so that isolator opening can pass through it.

Figure 37:
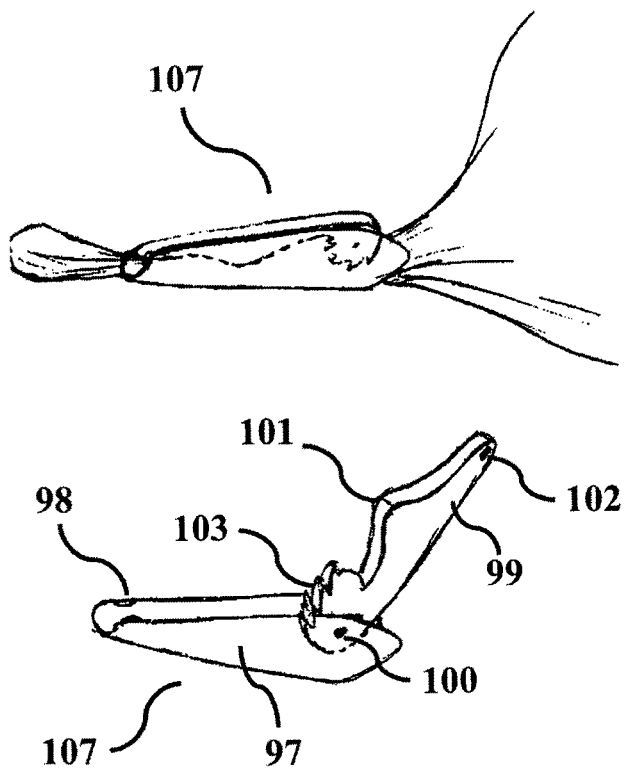

In yet another embodiment as shown in FIG. 37, closure element 107 may contain at least two parts—the body 97 and latch section 99. The body of the closure element may have a lock snap 98 and hinge pin 100. The latch may have locking/sealing teeth 103, hinge pin 100 to assemble with the body and a locking dimple feature 102 to lock with snap 98 in the body 97. The isolator opening can be compressed between latch teeth 103, hood feature 101 and the body surface to seal the opening. The lock snap 98 can hold the latch 99 tightly to complete the closing procedure.

Figure 38:
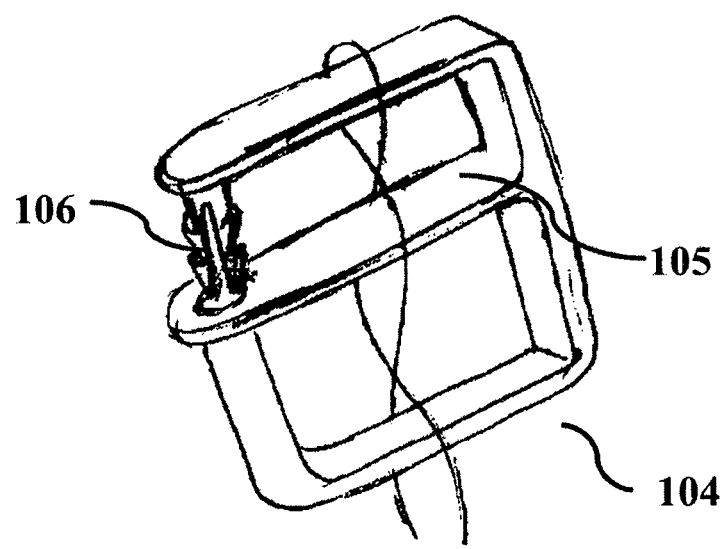

In another embodiment of the invention, shown in FIG. 38, the isolator can be twisted around at least one closure element which is a clamp 104. The clamp can be elongated with a frame formed by two sides, a top support member, middle member and bottom member extending transverse to create two openings 105, and the isolator weaving through the openings and around the top and bottom support members. On placement of the isolator in the clamp, it can be pressed into a lock 106 thereby closing the opening of the isolator.

In another embodiment of the invention, at least one adhesive tape/sticker may be provided with the isolator as closure element. User can remove peel-off paper from the adhesive tape and apply on the opening to permanently seal it. This can also avoid reusing of isolator.

Various other embodiments are described herewith for tissue insertion, morcellation and extraction using the isolator.

Figure 39:
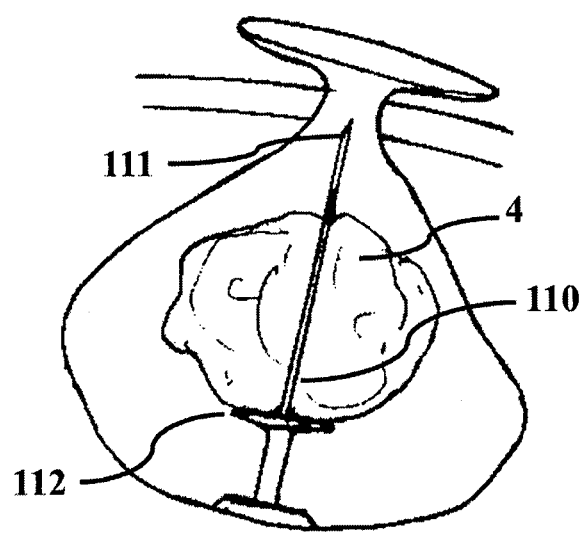
FIGS. 39 and 40 illustrate various embodiments of the present invention.

In one embodiment of the invention, illustrated by FIG. 39, the isolator may have a rod 110 attached to the center or off center of the isolator with a sharp tip 111 meant for piercing the tissue. The central rod can have a stopper 112 on it to prevent any tissue from sliding down towards the isolator once the tissue is mounted on the rod. The stopper can maintain a safe distance between the tissue and the isolator body and keep the morcellator blade away from the isolator body thereby preventing damage to the isolator. The morcellator may optionally have an external guide tube, which can be guided over the rod to cut tissue 4 without damaging the isolator.

Figure 40:
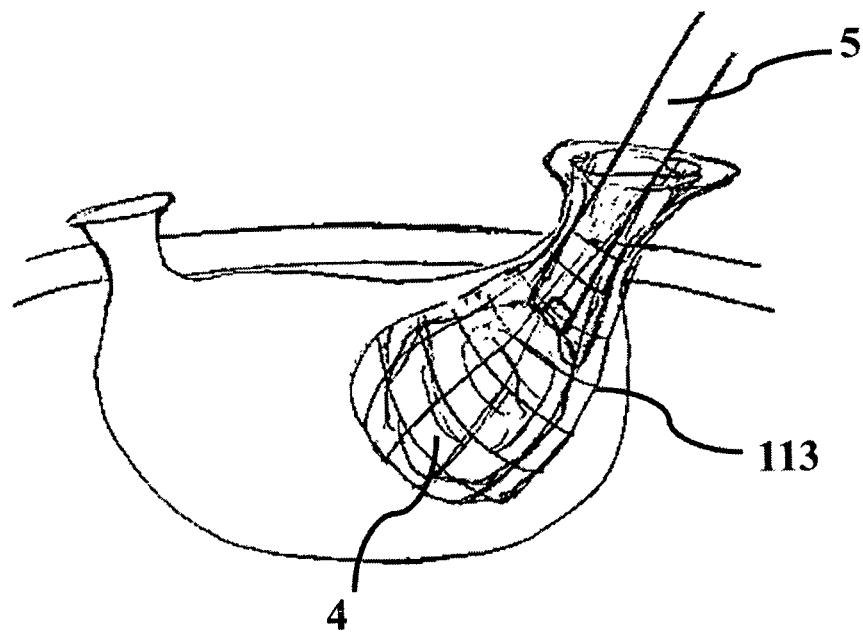

In accordance to yet another embodiment of the invention, illustrated by FIG. 40, the isolator may be made up of two disjoint layers. The outer layer may be made of an elastic material and the inner layer may be made of wire mesh 113. Tissue 4 can be placed inside the inner wire mesh 113. The isolator opening can be then taken out through the abdominal port. Before morcellation, gas can be passed into the outer layer to inflate it. The morcellator 5 can be passed into the mesh 113 to morcellate the tissue 4. Morcellation of tissue inside the inner mesh can avoid accidental cut or damage of the isolator by the morcellator or instrument. Wire mesh can act as a pushing/pulling element to aid in morcellation of the tissue. Thus it can avoid spillage of the small cut tissue from the isolator.

Figure 41:
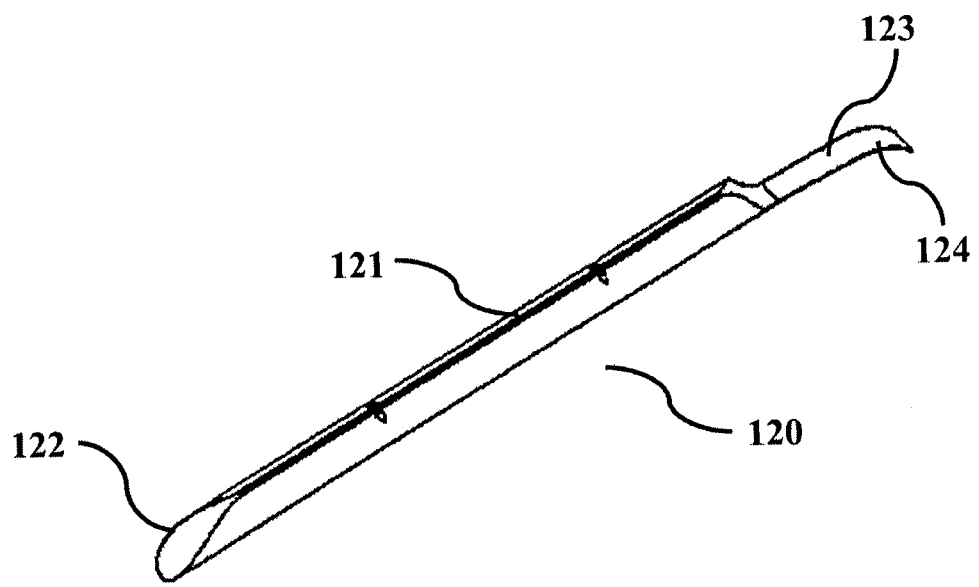
FIG. 41 illustrates introducer of the present invention

As illustrated in FIG. 41, an optional introducer may be supplied with the isolator for easy introduction of the isolator inside the body. The introducer 120 may be an elongated member. It may have a slit 121 on its body for placement of the isolator 1 in a folded condition.

The distal end 122 of the introducer 120 may be beveled or tapered so as to minimize the force required during insertion. The proximal end 124 may have a gripping feature which may be a single tail 123 like feature or it may have multiple tails to easily hold and pull it out once the isolator 1 is delivered inside the body cavity. Optionally the introducer may have markings for easy identification during use.

Figure 42:
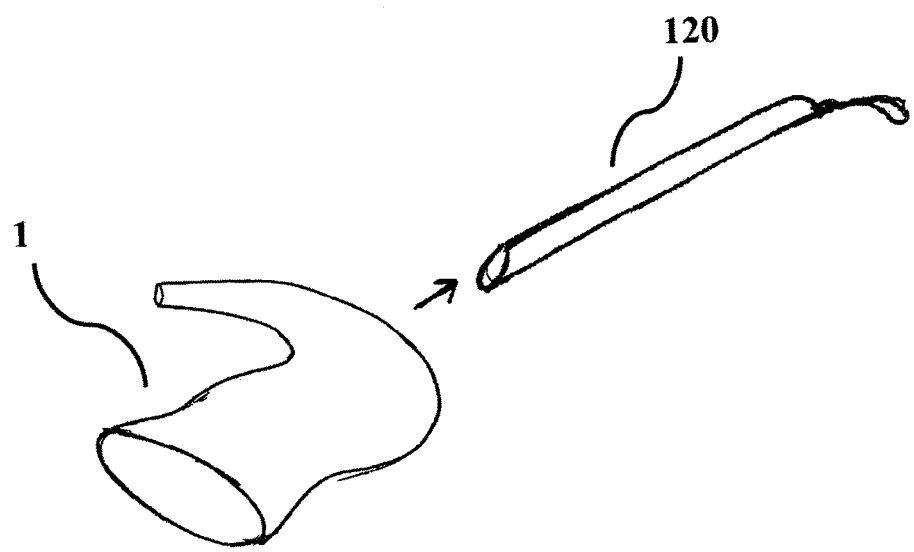
FIGS. 42 to 48 illustrate a method of using tissue isolator with optional introducer of the present invention.
Figure 43:
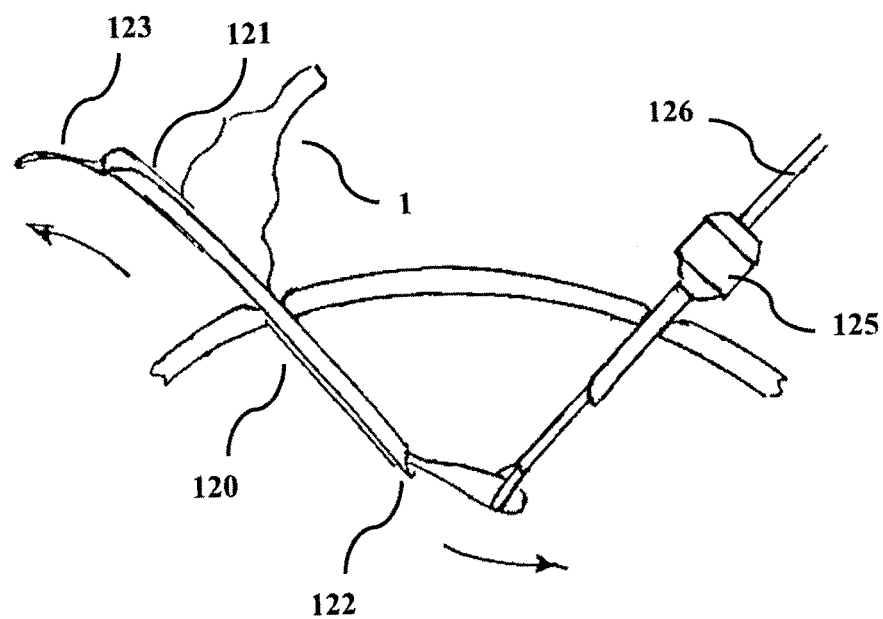
Figure 44:
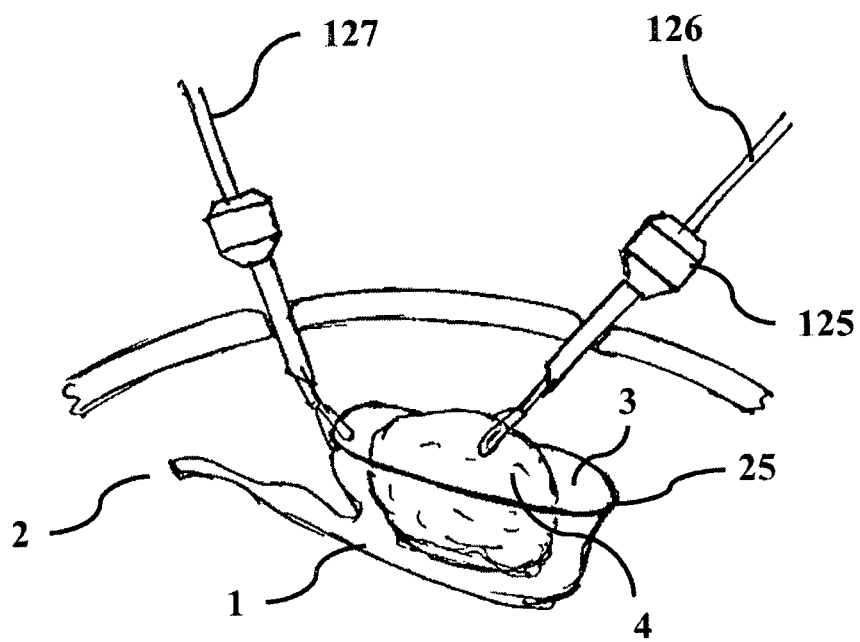
Figure 45:
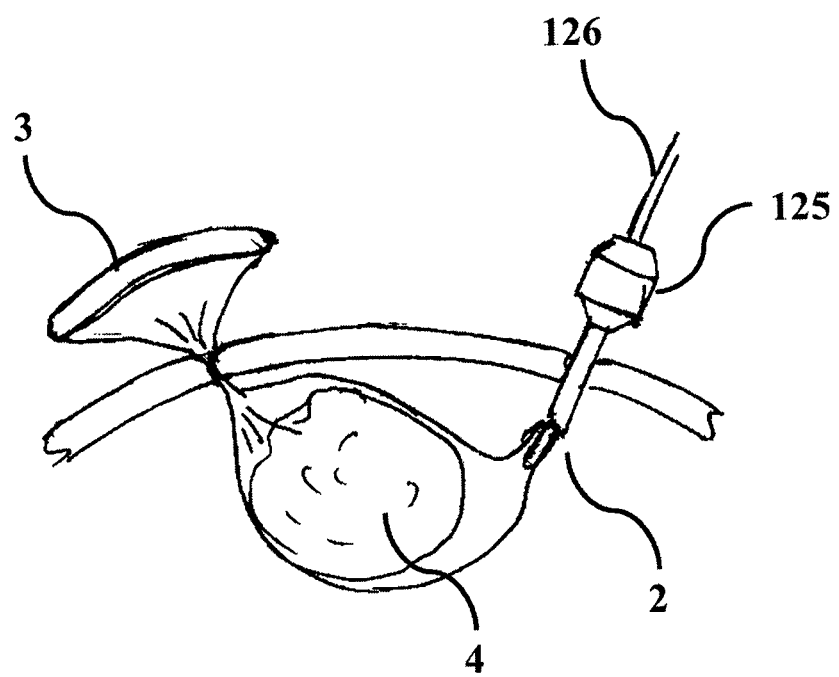

The following description provides for a method of isolation. FIG. 42 shows the isolator with openings and an introducer 120. The isolator 1 in folded form or rolled form can be placed inside the introducer such that a portion of the opening of the isolator may be exposed beyond the distal end of the introducer as shown in FIG. 42. The introducer 120 with the folded isolator may then be introduced inside the abdomen as shown in FIG. 43 and the abdomen can be filled with gas. The isolator can be then be pulled out of the introducer 120 leaving the isolator completely inside the body by pulling it with a grasper 126 that is inserted into the body from the other port 125, as shown in FIG. 43. The introducer can then be removed from the body. The opening of the isolator can be self-opening due to a flexible element such as flexible element 27 (FIG. 9). The tissue 4 can then be placed inside the opening of the isolator with a grasper 126 as shown in FIG. 44. The opening can be grasped with a grasper 127 and pulled out of the body such that the tissue 4 is contained inside the isolator as shown in FIG. 45.

Figure 46:
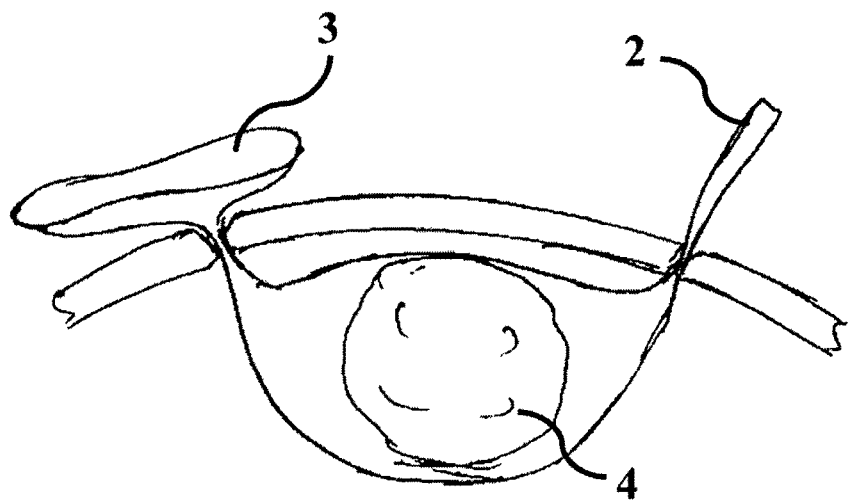
Figure 47:
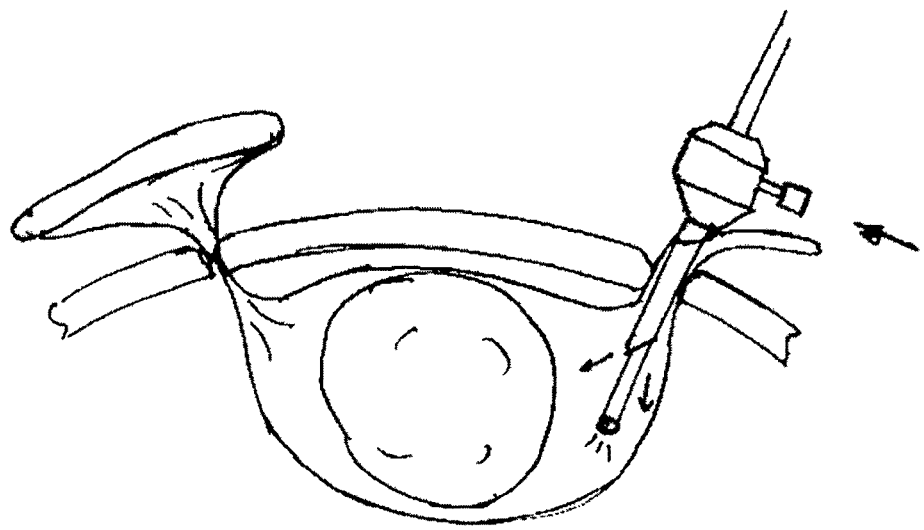

The openings are now outside the body as shown in FIG. 46. If there are more openings to the isolator, all or any of the openings may be taken out of the body or may be left inside or the openings may be closed state 52 (FIG. 17) to be formed later as per requirement. Orientation of the openings of the isolator which are outside the body can be checked and twisting, if found, can be removed by adjusting the orientation of the openings suitably as per the identification mark 33 as shown in FIG. 12. A trocar 125 can be passed through the opening as shown in FIG. 47 that seals the opening 2 of the isolator and the isolator can be insufflated. A laparoscope 7 can be passed through the trocar 125 for visualization. A tissue morcellator can be passed through the opening 3 of the isolator. Due to elasticity of the material or optional trocar, the gas leakage from the isolator can be prevented thereby providing a clear work area to perform morcellation, cutting or shredding of the tissue. The tissue 4 can be morcellated inside the isolator and the morcellated pieces can be taken out of the body using grasper passed through the morcellator. After morcellation is complete, the morcellator can be taken out from the opening, and the trocar and laparoscope can be taken out from the other opening, the isolator can then be deflated and the opening can be closed by closure element described above or by various other embodiments as illustrated above. Closing of the opening ensures that residual tissue fragments and/or tissue fluids and/or blood, if any, contained within the isolator after completion of morcellation will not leak out into the body. The isolator can then be manually pulled out of the body by holding the other opening.

The isolator in any of the embodiments may be supplied as pre-packaged within the introducer or it may be folded and placed into the introducer at the time of surgery.

Figure 48:
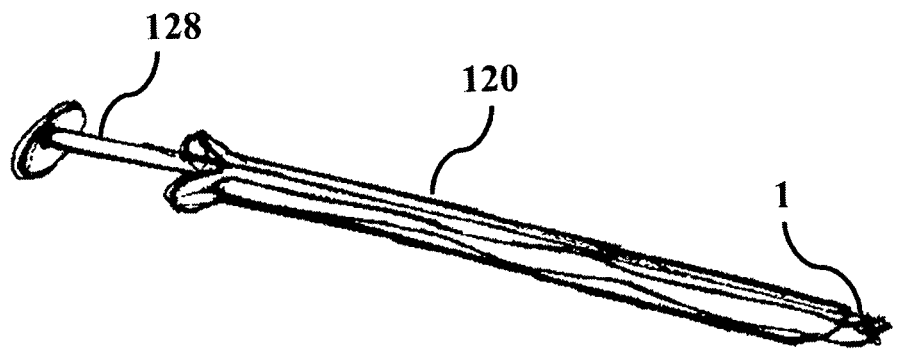

In another embodiment of the introducer, shown in FIG. 48, the isolator 1 may be contained inside an introducer 120. A pusher 128 may be placed inside the introducer. The pusher 128 can push the isolator into the body cavity. The pusher 128 may be releasably attached onto the opening of the isolator.

In another embodiment of the introducer, the introducer may have quick release live hinge linearly for easy opening and closing. This may provide for easy insertion of isolator inside introducer.

In various embodiments below, methods and device structures are described for pulling the isolator.

Figure 49:
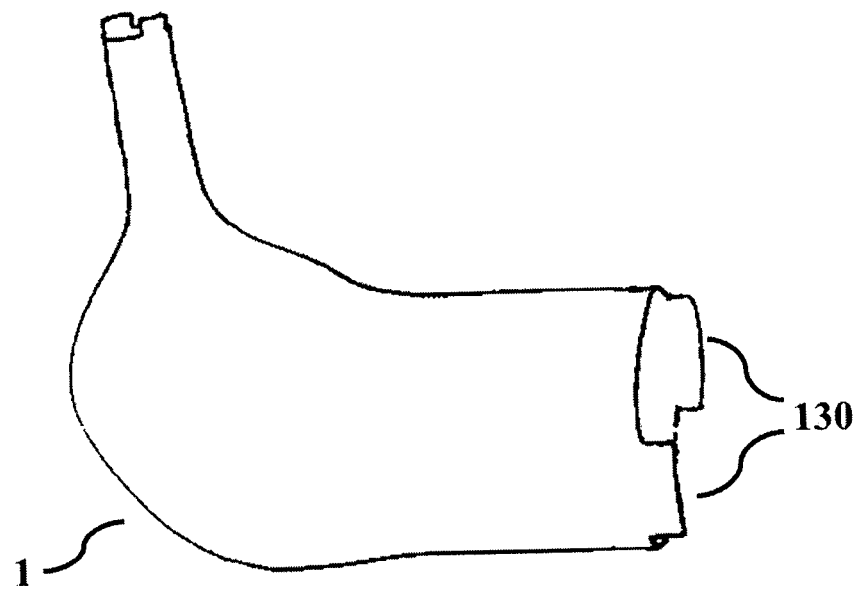
FIGS. 49 to 56 illustrate various embodiments of pulling elements.

In accordance to one embodiment of the invention, various pulling elements of the isolator opening have been mentioned which may have at least one grasping feature such as holding ring, hook or tab which may be used to manipulate the isolator. As shown in FIG. 49, the opening may have one or more staggered lips 130 extending outward from the top edge of the opening.

This may help the user to pick only one edge at a time using a grasper. Markings on the edges may help to distinguish between the top edge and the underlying edge.

Figure 50:
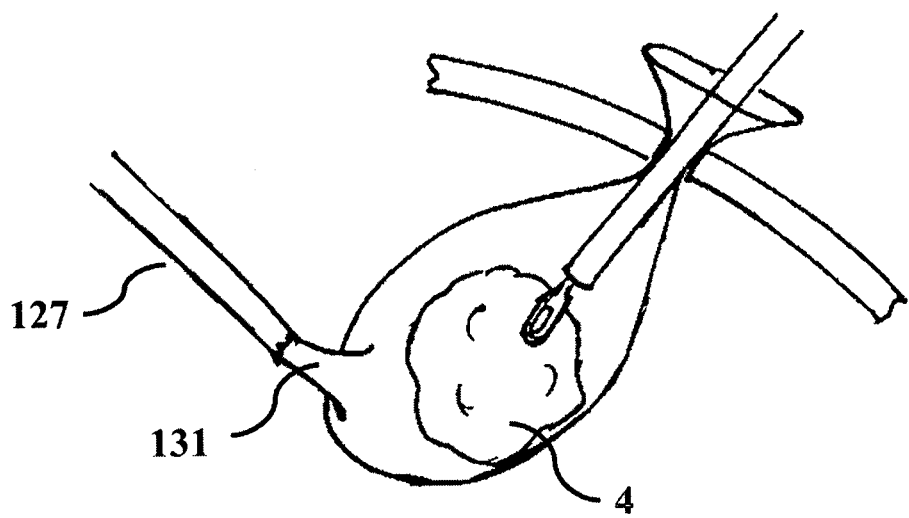

In yet another embodiment of the invention, the isolator may have at least one protruded structure 131 made up of the same material bonded at critical points all over or in some parts over its body. This may allow easy grasping and manipulation of the isolator within the peritoneum. As shown in FIG. 50, the isolator may have one or multiple protruded structure 131, which may help in easy holding of the isolator by grasper 127 and pulling out from abdominal port.

Figure 51:
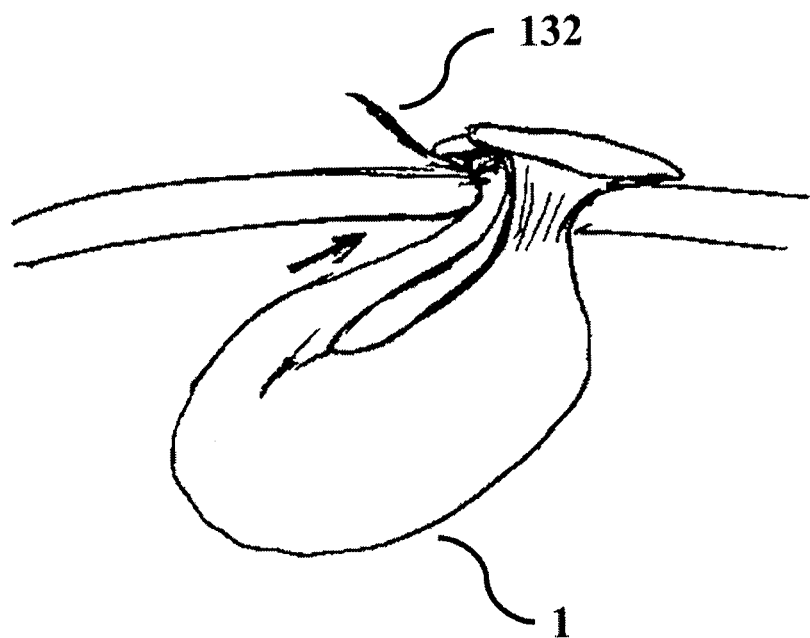

In yet another embodiment of the invention, shown in FIG. 51, the isolator may have a thread 132 attached to its opening to help in identifying and pulling out the opening; the opening may be used from any of the abdominal ports as required and the opening may be pulled from any of the ports.

Figure 52:
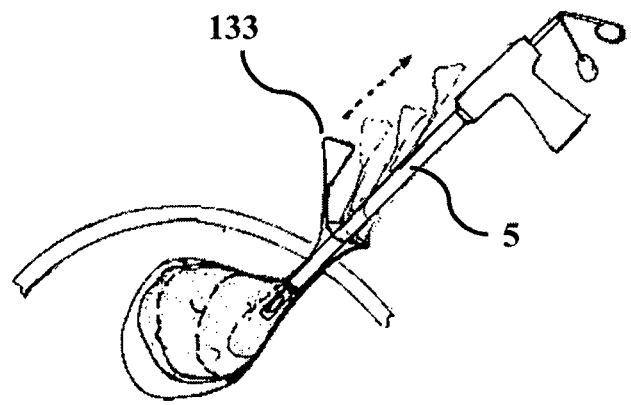

In yet another embodiment of the invention, shown in FIG. 52, the shape of the isolator may be such that the tissue can be maintained tangential to the morcellator 5. The free end of the isolator may have at least one attachment 133 to be pulled along the axis of the morcellator 5 during morcellation so that the isolator forces the tissue to be always tangential to the morcellator and the size of the isolator decreases with the decreasing size of the tissue. Advantage can be that, a separate instrument may not be needed to manipulate the tissue as the isolator itself can be used to manipulate the tissue.

There are various embodiments illustrated below for placement of tissue into the isolator and for insertion of isolator into the abdomen.

Figure 53:
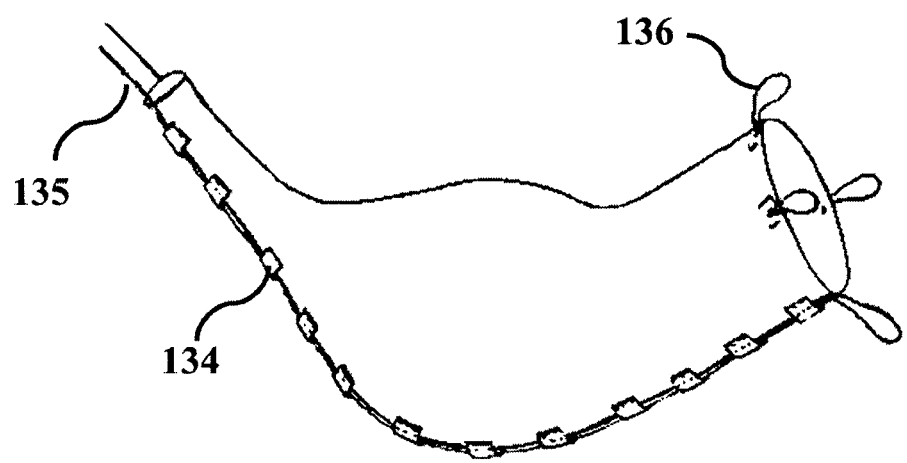
Figure 54:
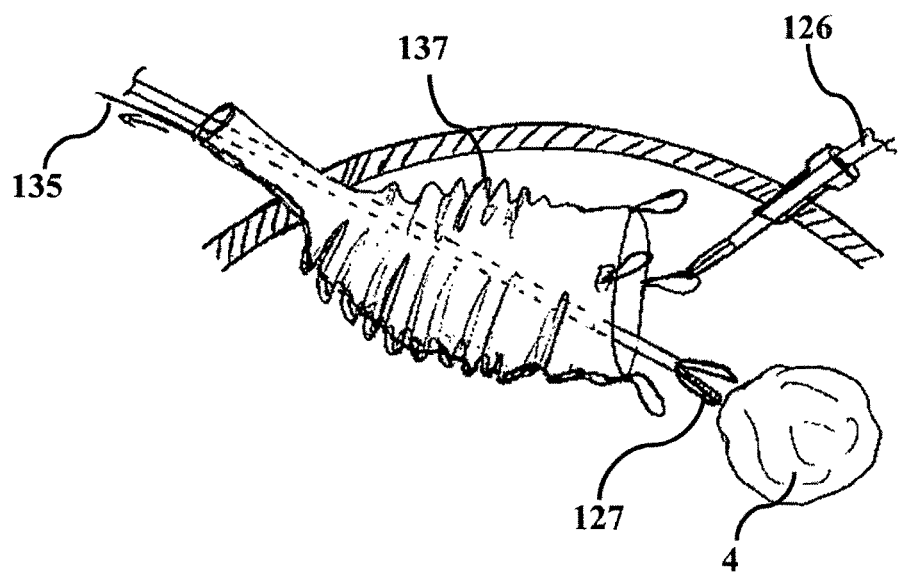
Figure 55:
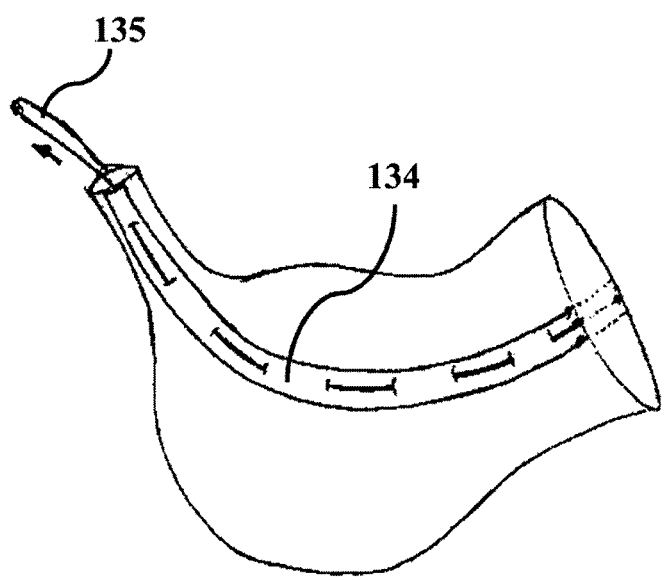

In yet another embodiment of the invention, shown in FIG. 53, and FIG. 55 a pull thread 135 may be passed through support strips 134 attached to the isolator. Support strips are loop like feature to receive the thread. Support strips may be part of the isolator or attached to the isolator. The support strips may be continuous or intermittent. Optionally the pull thread 135 may be attached at the opening of the isolator which forming a loop 136. As shown in FIG. 54, a grasper 126 may be introduced through the isolator and the pull thread 135 may be pulled to crumple 137 the isolator, which can help in easy exit of the grasper tip from the opening. There may be single or multiple loops at the opening, the user can hold these loops with the grasper to stabilize the opening while pulling the tissue 4 inside the isolator. The support strips, may help the isolator to regain its shape when gas is passed into the isolator or otherwise. The support strips may be placed along the edge of the isolator.

Figure 56:
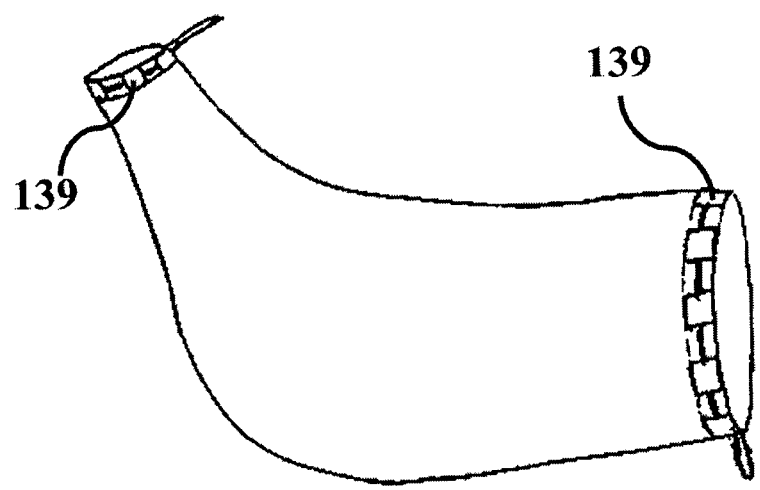

According to another embodiment of the invention, shown in FIG. 56, the isolator opening may have a split passage 139 for the purse string. This limited spilt passage 139 may decrease total volume of the folded isolator thereby helping in easy passage of the isolator through the abdominal port.

Figure 57:
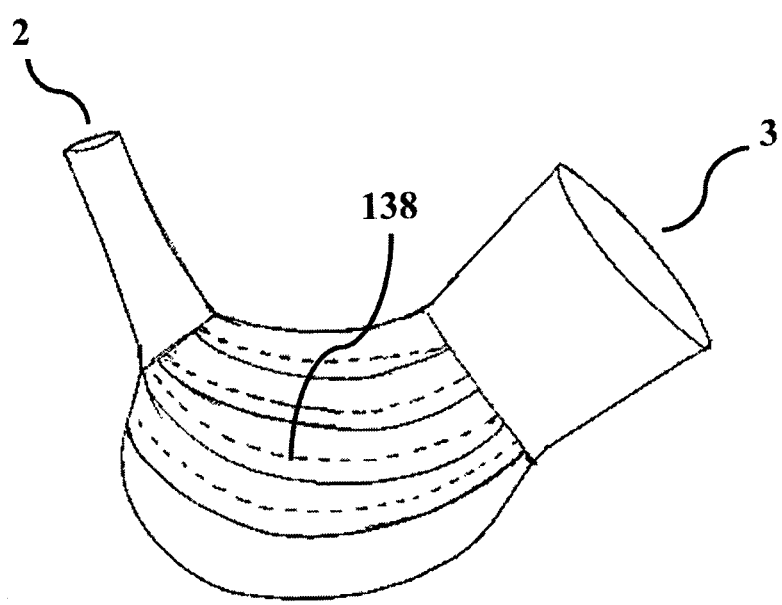
FIG. 57 illustrates embodiment for shape of isolator.

In an embodiment of the invention, shown in FIG. 57, to create more space for the working area inside the abdomen, the isolator central body portion may be in the form of bellow 138. The bellow may be along the axis of the isolator or perpendicular to the axis of the isolator or circular on either walls of the isolator. On inflating the isolator, these bellow type surfaces on both sides of the central section can expand to create more space.

An alternative method is described below for performing the procedure of insertion, morcellation and removal of isolator.

Figure 58:
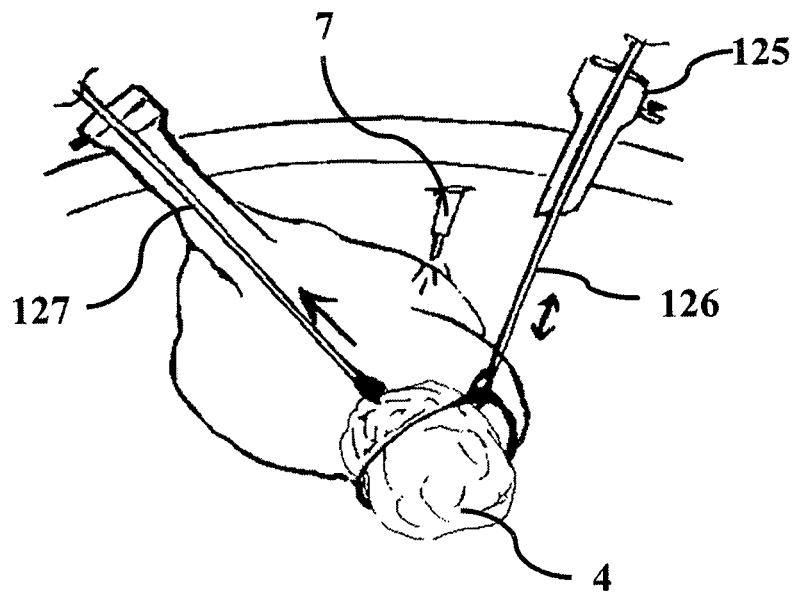
FIGS. 58, 59 illustrate various embodiments for method of tissue insertion inside isolator.
Figure 59:
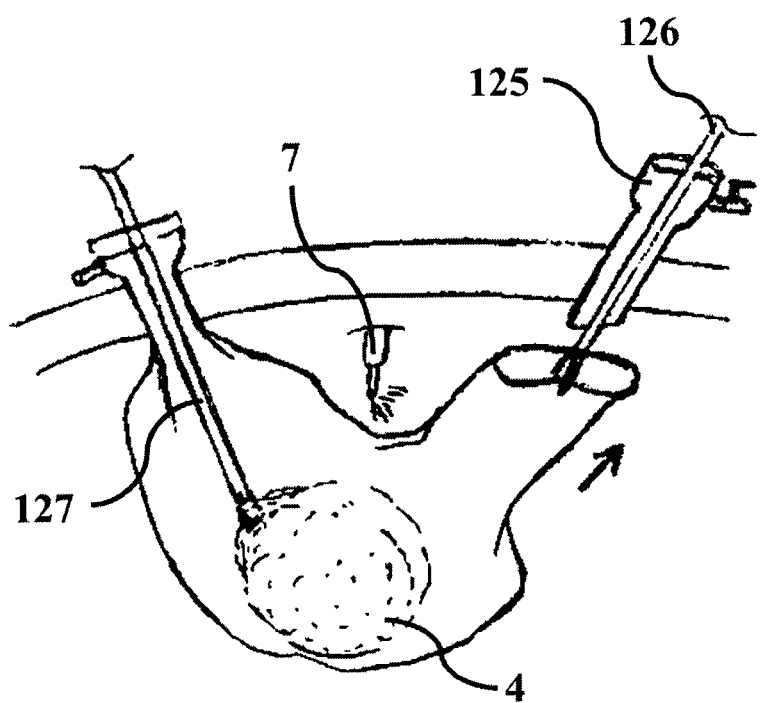

The isolator with openings may be passed into the abdomen filled with gas. A grasper or similar instrument may be used to hold the opening and pass it through the abdominal port. Another grasper is passed through another abdominal port may be used to pull the isolator inside the abdomen wherein the other opening may or may not be pulled inside the abdomen. Thereafter, one of the grasper 126 (FIG. 58) can hold the opening of the isolator to create clear passage for separated tissue. A grasper 127 or similar instrument can be passed through another opening of the isolator to grasp the tissue. The tissue 4 can then be pulled inside the isolator through the opening as shown in FIG. 58. Thereafter, the grasper on the other side can pull the opening out through the abdominal port as shown in FIG. 59. Supporting grasper 127 may be passed through the opening of the isolator. Laparoscope 7 may be passed through other port in the abdomen. After taking out opening of the isolator, through another abdominal port, the morcellator can be passed through it. Morcellation and subsequent steps of closing the isolator may be similar to as described elsewhere in this disclosure.

Figure 60:
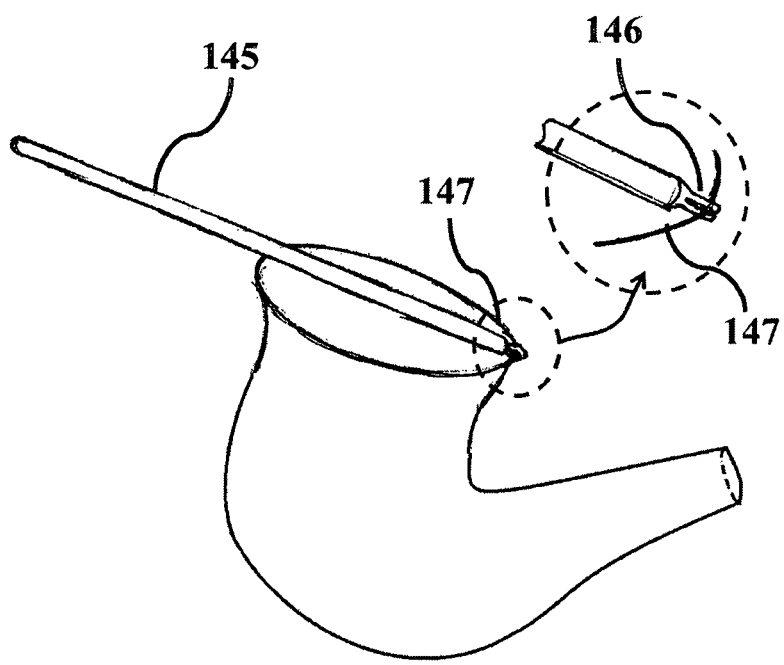
FIGS. 60 to 62 illustrate various embodiments of the deployer of tissue isolator of the present invention.

In another embodiment of the invention, shown in FIG. 60, the deployer 145 may have a grasper-like tip 146 capable of holding onto the edge of the opening 147 of the isolator. The tip can releasably latch onto the said edge of opening. It can remain latched until the deployer 145 pushes the isolator inside the body cavity. Once the isolator is inside the body cavity, the deployer 145 can be triggered so as to release the opening of the isolator.

Figure 61:
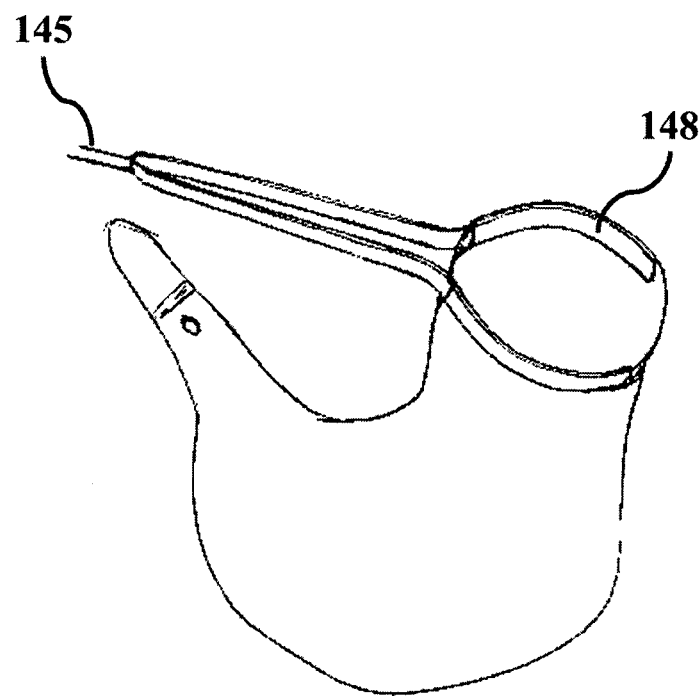

In another embodiment of the deployer, shown in FIG. 61, the deployer 145 may be flat shaped made of metal or plastic, where its distal end may be curved fork 148 and proximal end may have gripping handle.

Figure 62:
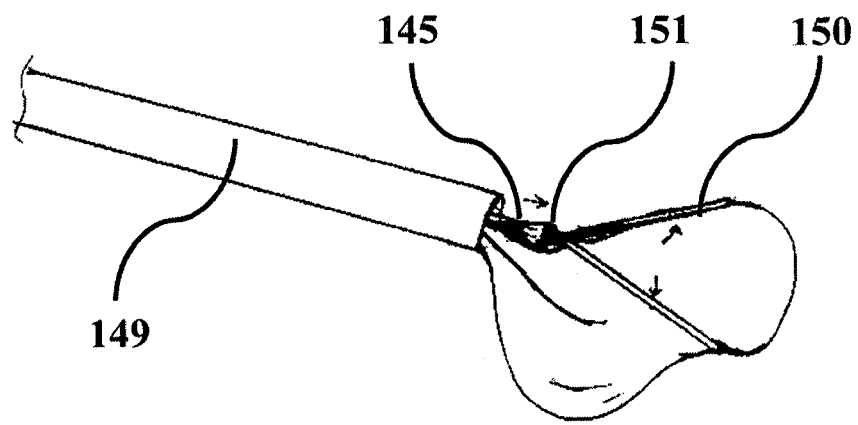

In another embodiment of the deployer, shown in FIG. 62, the deployer 145 may have fork end 150 with linkages 151 controlled by the actuator or knob at the proximal end of deployer 145.

This embodiment may help in easy placement of tissue inside the isolator. Isolator with deployer 145 may be inserted inside the tube 149 and then pushed out as shown in FIG. 62.

Figure 63:
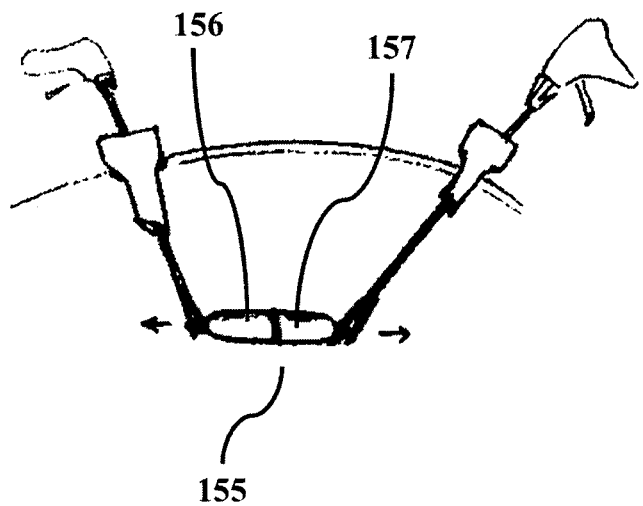
FIGS. 63 to 65 illustrate various embodiments for configuration for packing of isolator.
Figure 64:
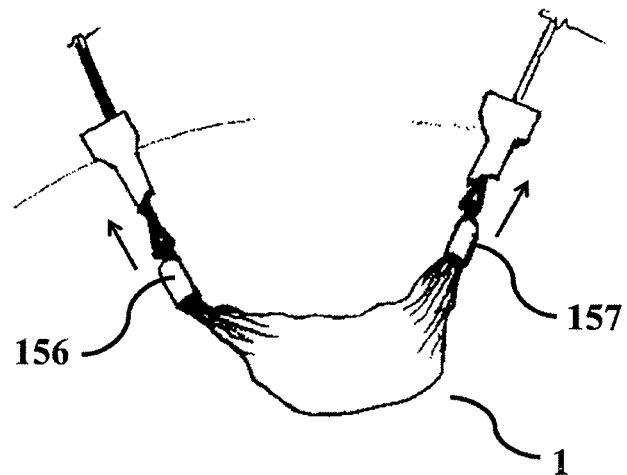

In yet another embodiment of the invention, shown in FIG. 63, isolator may be packed in capsule 155 with at least two halves and passed through a trocar port into the abdominal cavity. Once the cavity the two halves 156, 157 of the capsule can be separated from each other with the help of two graspers, exposing the isolator as shown in FIG. 63. The two halves of the capsule 155 can be taken outside the abdominal cavity as shown in FIG. 64.

Figure 65:
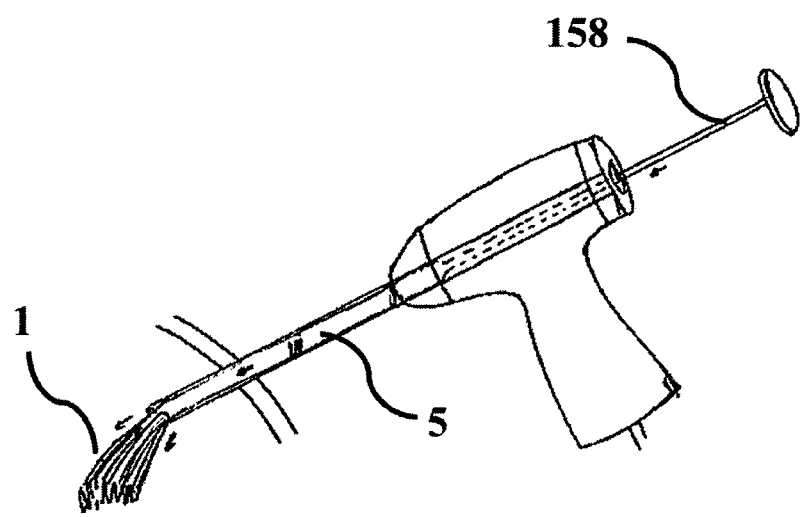

In yet another embodiment of the invention, illustrated by FIG. 65, the isolator 1 may be securely packed inside the morcellator 5. This may help to supply isolator and morcellator together and aid in ease of use. After separating tissue, the morcellator can be passed through preferably 10 to 18 mm port. The obturator 158 can push the isolator inside the abdomen for further use.

While the present invention has been illustrated by the description of the various embodiments thereof, and while the embodiments have been described in considerable detail, it is not intended to restrict or in any way limit the scope of the appended claims to such detail.

Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of applicant's general inventive concept.

The invention claimed is:

1. A tissue isolator comprising:
a central body portion forming an interior space configured to receive tissue;
a first neck and a second neck, each integrally formed with the central body portion and having a proximal end extending outwardly from the central body portion toward a distal end, the first neck and the second neck each being tubularly shaped over at least a portion of a length thereof, and each having a diameter, at some location along the length thereof, less than a diameter of the central body portion; and
a first opening and a second opening, the first opening located at a distal portion of the first neck and the second opening located at a distal end of the second neck, wherein the first neck and the second neck extend outwardly from the central body portion so that the distal end of both the first neck and the second neck are located above the central body portion when the tissue isolator is positioned for use;
wherein the first neck includes a tail distally located relative to the first opening and forming a distal end of the first neck, the tail configured to be held by a user during insertion of a trocar through the first opening.

2. The tissue isolator of claim 1, wherein a shape of the tissue isolator, from the distal end of the first neck, through the central body portion, to the distal end of the second neck, is U-shaped, L-shaped, or J-shaped.

3. The tissue isolator of claim 1, wherein the second opening has a diameter greater than the diameter of the second neck.

4. The tissue isolator of claim 1, where at least one of the first and the second openings include a flexible element having shape memory, where deformation of the respective opening to any shape results, after release, to a return of the respective opening to an original, natural shape, wherein the flexible element is nitinol formed in a wire or loop, or nitinol or spring steel wire formed in a zig-zag form.

5. A tissue isolator comprising:
a central body portion forming an interior space configured to receive tissue;
a first neck and a second neck, each integrally formed with the central body portion and having a proximal end extending outwardly from the central body portion toward a distal end, the first neck and the second neck each being tubularly shaped over at least a portion of a length thereof, and each having a diameter, at some location along the length thereof, less than a diameter of the central body portion;
a first opening and a second opening, the first opening located at a distal portion of the first neck and the second opening located at a distal end of the second neck, wherein the first neck and the second neck extend outwardly from the central body portion so that the distal end of both the first neck and the second neck are located above the central body portion when the tissue isolator is positioned for use; and
multiple markings illustrating a representative shape of the tissue isolator to identify position and orientation of the tissue isolator.

6. A tissue isolator comprising:
a central body portion forming an interior space configured to receive tissue;
a first neck and a second neck, each integrally formed with the central body portion and having a proximal end extending outwardly from the central body portion toward a distal end, the first neck and the second neck each being tubularly shaped over at least a portion of a length thereof, and each having a diameter, at some location along the length thereof, less than a diameter of the central body portion;
a first opening and a second opening, the first opening located at a distal portion of the first neck and the second opening located at a distal end of the second neck, wherein the first neck and the second neck extend outwardly from the central body portion so that the distal end of both the first neck and the second neck are located above the central body portion when the tissue isolator is positioned for use; and
markings to identify position and orientation of the tissue isolator, the markings including at least multiple, parallel lines longitudinally arranged on the second neck to indicate any twisting of the tissue isolator at the second opening.

7. A tissue isolator comprising:
a central body portion forming an interior space configured to receive tissue;
a first neck and a second neck, each integrally formed with the central body portion and having a proximal end extending outwardly from the central body portion toward a distal end, the first neck and the second neck each being tubularly shaped over at least a portion of a length thereof, and each having a diameter, at some location along the length thereof, less than a diameter of the central body portion;
a first opening and a second opening, the first opening located at a distal portion of the first neck and the second opening located at a distal end of the second neck, wherein the first neck and the second neck extend outwardly from the central body portion so that the distal end of both the first neck and the second neck are located above the central body portion when the tissue isolator is positioned for use; and
markings to identify position and orientation of the tissue isolator, the markings including at least directional markings indicating a direction of each of the first and the second opening.

8. A tissue isolator comprising:
a central body portion forming an interior space configured to receive tissue;
a first neck and a second neck, each integrally formed with the central body portion and having a proximal end extending outwardly from the central body portion toward a distal end, the first neck and the second neck each being tubularly shaped over at least a portion of a length thereof, and each having a diameter, at some location along the length thereof, less than a diameter of the central body portion;

a first opening and a second opening, the first opening located at a distal end of the first neck and the second opening located at a distal end of the second neck, wherein the first neck and the second neck extend outwardly from the central body portion so that the distal end of both the first neck and the second neck are located above the central body portion when the tissue isolator is positioned for use; and markings to identify position and orientation of the isolator, the markings including at least multiple, parallel lines longitudinally arranged on the second neck to indicate any twisting of the tissue isolator at the second opening.

9. The tissue isolator of claim 8, wherein a shape of the tissue isolator, from the distal end of the first neck, through the central body portion, to the distal end of the second neck, is U-shaped, L-shaped, or J-shaped.

10. The tissue isolator of claim 8, wherein the first opening has a diameter greater than the diameter of the first neck and the second opening has a diameter greater than the diameter of the second neck.

11. The tissue isolator of claim 8, wherein at least one of the first and the second openings include a flexible element having shape memory, where deformation of the respective opening to any shape results, after release, to a return of the respective opening to an original, natural shape.

12. A tissue isolator comprising:
a central body portion forming an interior space configured to receive tissue;
a first neck and a second neck, each integrally formed with the central body portion and having a proximal end extending outwardly from the central body portion toward a distal end, the first neck and the second neck each being tubularly shaped over at least a portion of a length thereof, and each having a diameter, at some location along the length thereof, less than a diameter of the central body portion;
a first opening and a second opening, the first opening located at a distal end of the first neck and the second opening located at a distal end of the second neck, wherein the first neck and the second neck extend outwardly from the central body portion so that the distal end of both the first neck and the second neck are located above the central body portion when the tissue isolator is positioned for use; and
multiple markings illustrating a representative shape of the tissue isolator to identify position and orientation of the tissue isolator.

13. A tissue isolator comprising:
a central body portion forming an interior space configured to receive tissue;
a first neck and a second neck, each integrally formed with the central body portion and having a proximal end extending outwardly from the central body portion toward a distal end, the first neck and the second neck each being tubularly shaped over at least a portion of a length thereof;
a first opening and a second opening, the first opening located at a distal portion of the first neck and the second opening located at a distal end of the second neck, the second opening having a diameter greater than the diameter of the second neck;
wherein the first neck includes a tail distally located relative to the first opening and forming a distal end of the first neck, the tail configured to be held by a user during insertion of a trocar through the first opening.

14. The tissue isolator of claim 13, wherein the first neck and the second neck each have a diameter, at some location along the length thereof, less than a diameter of the central body portion.

15. The tissue isolator of claim 13, wherein the second opening has a diameter greater than the diameter of the first neck and of the second neck.

16. The tissue isolator of claim 13, wherein a shape of the tissue isolator, from the distal end of the first neck, through the central body portion, to the distal end of the second neck, is U-shaped, L-shaped, or J-shaped.

17. The tissue isolator of claim 13, wherein the first neck and the second neck extend outwardly from the central body portion so that the distal end of both the first neck and the second neck are located above the central body portion when the tissue isolator is positioned for use.

18. The tissue isolator of claim 13, wherein at least one of the first and the second openings include a flexible element having shape memory, where deformation of the respective opening to any shape results, after release, to a return of the respective opening to an original, natural shape.

19. A tissue isolator comprising:
a central body portion forming an interior space configured to receive tissue;
a first neck and a second neck, each integrally formed with the central body portion and having a proximal end extending outwardly from the central body portion toward a distal end, the first neck and the second neck each being tubularly shaped over at least a portion of a length thereof;
a first opening and a second opening, the first opening located at a distal portion of the first neck and the second opening located at a distal end of the second neck, the second opening having a diameter greater than the diameter of the second neck; and
markings illustrating a representative shape of the tissue isolator to identify position and orientation of the tissue isolator.

20. A tissue isolator comprising:
a central body portion forming an interior space configured to receive tissue;
a first neck and a second neck, each integrally formed with the central body portion and having a proximal end extending outwardly from the central body portion toward a distal end, the first neck and the second neck each being tubularly shaped over at least a portion of a length thereof;
a first opening and a second opening, the first opening located at a distal portion of the first neck and the second opening located at a distal end of the second neck, the second opening having a diameter greater than the diameter of the second neck; and
markings to identify position and orientation of the tissue isolator, the markings including at least multiple, parallel lines longitudinally arranged on the second neck to indicate any twisting of the tissue isolator at the second opening.

21. A tissue isolator comprising:
a central body portion forming an interior space configured to receive tissue;
a first neck and a second neck, each integrally formed with the central body portion and having a proximal end extending outwardly from the central body portion toward a distal end, the first neck and the second neck each being tubularly shaped over at least a portion of a length thereof;

a first opening and a second opening, the first opening located at a distal portion of the first neck and the second opening located at a distal end of the second neck, the second opening having a diameter greater than the diameter of the second neck; and markings to identify position and orientation of the tissue isolator, the markings including at least directional markings indicating a direction of each of the first and the second opening.

\* \* \* \* \*